US010508131B2

(12) United States Patent
Cox et al.

(10) Patent No.: US 10,508,131 B2
(45) Date of Patent: Dec. 17, 2019

(54) CYSTEINE ANALOGS OF EXENDIN-4

(71) Applicant: Bolder Biotechnology, Inc., Boulder, CO (US)

(72) Inventors: George N. Cox, Louisville, CO (US); Mary S. Rosendahl, Broomfield, CO (US)

(73) Assignee: Bolder Biotechnology, Inc., Boulder, CO (US)

( * ) Notice: Subject to any disclaimer, the term of this patent is extended or adjusted under 35 U.S.C. 154(b) by 0 days.

(21) Appl. No.: 15/816,827

(22) Filed: Nov. 17, 2017

(65) Prior Publication Data

US 2018/0334475 A1  Nov. 22, 2018

Related U.S. Application Data

(63) Continuation of application No. 15/049,246, filed on Feb. 22, 2016, now abandoned, which is a continuation of application No. 14/089,469, filed on Nov. 25, 2013, now Pat. No. 9,296,804, which is a continuation of application No. 12/519,203, filed as application No. PCT/US2007/087657 on Dec. 14, 2007, now Pat. No. 8,617,531.

(60) Provisional application No. 60/870,022, filed on Dec. 14, 2006.

(51) Int. Cl.
| | |
|---|---|
| *C07K 1/113* | (2006.01) |
| *C07K 14/575* | (2006.01) |
| *C07K 14/605* | (2006.01) |
| *C07K 14/645* | (2006.01) |
| *A61K 38/00* | (2006.01) |
| *C07K 14/57* | (2006.01) |
| *C07K 1/16* | (2006.01) |

(52) U.S. Cl.
CPC .......... *C07K 1/1136* (2013.01); *C07K 1/1133* (2013.01); *C07K 1/16* (2013.01); *C07K 14/57* (2013.01); *C07K 14/575* (2013.01); *C07K 14/605* (2013.01); *C07K 14/645* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,929,554 A | 5/1990 | Goeddel et al. | |
| 4,992,531 A | 2/1991 | Patroni et al. | |
| 5,096,705 A | 3/1992 | Goeddel et al. | |
| 5,206,344 A | 4/1993 | Katre et al. | |
| 5,223,407 A | 6/1993 | Wong et al. | |
| 5,574,137 A | 11/1996 | Gray et al. | |
| 5,582,824 A | 12/1996 | Goeddel et al. | |
| 5,595,888 A | 1/1997 | Gray et al. | |
| 5,690,925 A | 11/1997 | Gray et al. | |
| 5,766,897 A | 6/1998 | Braxton | |
| 5,849,535 A | 12/1998 | Cunningham et al. | |
| 6,046,034 A | 4/2000 | Waschutza et al. | |
| 6,248,564 B1 * | 6/2001 | Walter | C07K 14/70539 424/178.1 |
| 6,497,871 B1 | 12/2002 | Gray et al. | |
| 6,608,183 B1 * | 8/2003 | Cox, III | C07K 14/475 530/399 |
| 6,653,098 B1 | 11/2003 | Violand et al. | |
| 6,692,264 B2 | 2/2004 | Fuss | |
| 6,780,613 B1 | 8/2004 | Wells et al. | |
| 6,894,025 B2 | 5/2005 | Harris | |
| 7,038,015 B2 | 5/2006 | Jensen | |
| 7,230,081 B1 | 6/2007 | Jensen et al. | |
| 7,306,931 B2 | 12/2007 | Rosendahl et al. | |
| 7,959,909 B2 | 6/2011 | Cox | |
| 8,617,531 B2 | 12/2013 | Cox et al. | |
| 8,618,256 B2 | 12/2013 | Cox | |
| 8,932,828 B2 | 1/2015 | Rosendahl et al. | |
| 9,296,804 B2 | 3/2016 | Cox et al. | |
| 2003/0138403 A1 | 7/2003 | Drustrup | |
| 2008/0219950 A1 | 9/2008 | Cox | |
| 2009/0269804 A1 | 10/2009 | Rosendahl et al. | |

(Continued)

FOREIGN PATENT DOCUMENTS

| | | |
|---|---|---|
| CN | 1206716 | 2/1999 |
| EP | 0218374 | 4/1987 |
| EP | 0219874 | 4/1987 |

(Continued)

OTHER PUBLICATIONS

Campbell et al., "Pegylated peptides: V. Carboxy-terminal PEGylated analogs of growth hormone-releasing factor (GRF) display enhanced duration of biological activity in vivo," J Peptide Res, Jun. 1997, vol. 49, pp. 527-537.

Cardamone "Comparing the refolding and reoxidation of recombinant porcine growth hormone from a urea denatured state and from *Escherichia coli* inclusion bodies," Biochemistry, May 1995, vol. 34, pp. 5773-5794.

Chang et al. "High-level secretion of human growth hormone by *Escherichia coli*," Gene, 1987 vol. 55, pp. 189-196.

(Continued)

*Primary Examiner* — Elly-Gerald Stoica
(74) *Attorney, Agent, or Firm* — Sheridan Ross P.C.

(57) ABSTRACT

Disclosed is a method for refolding a protein or peptide that does not contain essential disulfides and that contains at least one free cysteine residue. Also disclosed are polymer IFN-γ conjugates that have been created by the chemical coupling of polymers such as polyethylene glycol moieties to IFN-γ, particularly via a free cysteine in the protein. Also disclosed are analogs of bioactive peptides that may be used to create longer acting versions of the peptides, including analogs of glucagon, glucagon-like peptide-1 (GLP-1), GLP-2, Gastric inhibitory peptide (GIP), PYY, exendin, ghrelin, gastrin, amylin, and oxyntomodulin.

14 Claims, No Drawings
Specification includes a Sequence Listing.

(56) References Cited

U.S. PATENT DOCUMENTS

2017/0015701 A1    1/2017  Cox et al.

FOREIGN PATENT DOCUMENTS

| | | |
|---|---|---|
| EP | 0312358 | 4/1989 |
| EP | 0355460 | 2/1990 |
| EP | 0458064 | 11/1991 |
| JP | H04-504801 | 8/1992 |
| JP | H08-506095 | 7/1996 |
| JP | H10-234386 | 9/1998 |
| WO | WO 90/12874 | 11/1990 |
| WO | WO 93/00109 | 1/1993 |
| WO | WO 94/01453 | 1/1994 |
| WO | WO 94/12219 | 6/1994 |
| WO | WO 95/32003 | 11/1995 |
| WO | WO 99/03887 | 1/1999 |
| WO | WO 99/35248 | 7/1999 |
| WO | WO 99/42486 | 8/1999 |
| WO | WO 00/15796 | 3/2000 |
| WO | WO 00/42175 | 7/2000 |
| WO | WO 01/054981 | 8/2001 |
| WO | WO 01/087925 | 11/2001 |
| WO | WO 03/002152 | 1/2003 |
| WO | WO 2004/093823 | * 11/2004 |

OTHER PUBLICATIONS

Chene et al., "Crystallization of the Complex of Human IFN-gamma and the Extracellular Domain of the IFN-gamma Receptor," Proteins: Structure, Function, and Genetics, 1995, vol. 23, pp. 591-594.

Ealick et al., "Three-dimensional structure of recombinant human interferon-gamma," Science, May 3, 1991, vol. 252(5006), pp. 698-702.

Goodson et al., "Site-directed pegylation of recombinant interleukin-2 at its glycosylation site," Biotechnology, Apr. 1990, vol. 8(4), pp. 343-346.

Ishikawa et al., "The Substitution of Cysteine 17 of Recombinant Human G-CSF with Alanine Greatly Enhanced its Stability," Cell Structure and Function, 1992, vol. 17, pp. 61-65.

Jeong et al., "Secretory Production of Human Granulocyte Colony-Stimulating Factor in *Escherichia coli*," Protein Expression and Purification, 2001, vol. 23, Iss. 2, pp. 311-318.

Mozdzanowski, "Deblocking of Proteins Containing N-Terminal Pyroglutamic Acid ", Protein Sequencing Protocols, Methods in Molecular Biology, vol. 211, (Ed. Smith), Humana Press, 2003, pp. 365-369.

Ngo et al., The Protein Folding Problem and Tertiary Structure Prediction, 1994 (K. Merz., and S. Le Grand eds.), pp. 492-495.

Paetzel et al., "Signal peptide cleavage in the *E. coli* membrane," CSBMCB/SCBBMC Bulletin, Biochemistry & Molecular Biology, University of British Columbia, 2001, pp. 60-65.

Perez-Perez et al. "DNAK/DNAJ Supplementation Improves the Periplasmic Production of Human Granulocyte-Colony Stimulating Factor in *Escherichia coli*." Biochemical and Biophysical Res. Comm., May 16, 1995, vol. 210, No. 2, pp. 524-529.

Rariy et al., "Correct protein folding in glycerol," Proc Natl Acad Sci., Dec. 1997, vol. 94, pp. 13520-13523.

Sammons et al., "Ultrasensitive silver-based color staining of polypeptides in polyacrylamide gels," Electrophoresis, 1981, vol. 2, Iss. 3, pp. 135-141.

Watahiki, "Recombinant Teleost Growth Hormones: Syntheses in *Escherichia coli*, Purification, Pefolding and the Biological Activity," Mie Medical Journal, 1992, vol. 42(1), pp. 89-106.

Wells, "Additivity of mutational effects in proteins," Biochemistry, Sep. 1990, vol. 29(37), pp. 8509-8517.

Search Report and Written Opinion for International (PCT) Patent Application No. PCT/US07/87657, dated Sep. 23, 2008.

International Preliminary Report on Patentability for International (PCT) Patent Application No. PCT/US07/87657, dated Jun. 25, 2009.

Extended European Search Report for European Patent Application No. 07865717.8 dated Oct. 31, 2013, 7 pages.

Notice of Intention to Grant for European Patent Application No. 07865717.8 dated Feb. 27, 2015, 8 pages.

Notice of Intention to Grant for European Patent Application No. 07865717.8 dated Jul. 13, 2015.

Restriction Requirement for U.S. Appl. No. 12/519,203, dated Apr. 14, 2010.

Official Action for U.S. Appl. No. 12/519,203, dated Jul. 9, 2010.

Official Action for U.S. Appl. No. 12/519,203, dated Nov. 12, 2010.

Official Action for U.S. Appl. No. 12/519,203, dated Feb. 7, 2013, 12 pages.

Notice of Allowance for U.S. Appl. No. 12/519,203, dated Aug. 27, 2013, 9 pages.

Official Action for U.S. Appl. No. 14/089,469, dated Nov. 21, 2014 Restriction Requirement.

Official Action for U.S. Appl. No. 14/089,469, dated May 27, 2015, 14 pages.

Notice of Allowance for U.S. Appl. No. 14/089,469, dated Nov. 24, 2015, 7 pages.

Official Action for U.S. Appl. No. 15/049,246, dated Dec. 20, 2016 8 pages Restriction Requirement.

Official Action for U.S. Appl. No. 15/049,246, dated May 18, 2017 9 pages.

* cited by examiner

US 10,508,131 B2

CYSTEINE ANALOGS OF EXENDIN-4

CROSS REFERENCE TO RELATED APPLICATIONS

This application is a continuation of U.S. patent application Ser. No. 15/049,246, filed Feb. 22, 2016, now abandoned; which is a continuation of U.S. patent application Ser. No. 14/089,469, filed Nov. 25, 2013, now U.S. Pat. No. 9,296,804, issued Mar. 29, 2016; which is a continuation of U.S. patent application Ser. No. 12/519,203, filed Nov. 19, 2009, now U.S. Pat. No. 8,617,531, issued Dec. 31, 2013; which is a national stage application under 35 U.S.C. 371 of PCT Application No. PCT/US2007/087657, having an international filing date of Dec. 14, 2007, which designated the United States, which PCT application claimed the benefit of U.S. Application Ser. No. 60/870,022, filed Dec. 14, 2006; the entire disclosure of each of which is hereby incorporated herein by reference.

STATEMENT REGARDING GOVERNMENT INTERESTS

This invention was made with government support under grant numbers AI060043 and CA108001, each awarded by the National Institutes of Health. The government has certain rights in the invention.

REFERENCE TO SEQUENCE LISTING

This application contains a Sequence Listing submitted as an electronic text file named "4152-18-PUS-1-1-1_Sequence_Listing_ST25.txt", having a size in bytes of 8000 bytes, and created on 7 Aug. 2018. The information contained in this electronic file is hereby incorporated by reference in its entirety pursuant to 37 CFR § 1.52(e)(5).

FIELD OF THE INVENTION

This invention generally relates to novel polymer protein or peptide conjugates, and in a preferred embodiment, novel interferon gamma (IFN-γ) conjugates, that have been created by the chemical coupling of polymers such as polyethylene glycol moieties to variants of proteins and peptides, and methods of making and using such conjugates. The invention also relates to methods for producing proteins and peptides that lack essential disulfides and contain at least one free cysteine residue, such proteins including, but not limited to, IFN-γ.

BACKGROUND OF THE INVENTION

There is considerable interest on the part of patients and healthcare providers in the development of low cost, long-acting, "user-friendly" protein therapeutics. Proteins are expensive to manufacture and unlike conventional small molecule drugs, are not readily absorbed by the body. Therefore, proteins must be administered by injection. Most proteins are cleared rapidly from the body, necessitating frequent, often daily, injections. This is particularly the case for small peptides, which often have half-lives on the order of minutes following injections into humans. Patients dislike injections, which leads to reduced compliance and reduced drug efficacy. The length of time an injected protein remains in the body is finite and is determined by the protein's size and whether or not the protein contains covalent modifications such as glycosylation.

Introduction of proteins into circulation exposes the proteins to numerous cell types, enzymes and routes of extravasation that contribute to their rapid clearance or catabolism. The protein may be attacked by plasma proteases or bind plasma proteins or cell surface receptors. Either receptor-mediated or less specific binding may result in the uptake of the protein via endocytotic or pinocytotic mechanisms, with the end result being degradation by lysosomal proteases. Proteins that avoid capture by these cells may pass out of the circulation via uptake by the liver, the lymphatic system or renal glomeruli (Sheffield, 2001).

Circulating concentrations of injected proteins change constantly, often by several orders of magnitude, over a 24 hour period. Rapidly changing concentrations of protein agonists can have dramatic downstream consequences, at times understimulating and at other times overstimulating target cells. Similar problems plague protein antagonists. These fluctuations can lead to decreased efficacy and increased frequency of adverse side-effects for protein therapeutics. The rapid clearance of recombinant proteins from the body significantly increases the amount of protein required per patient and dramatically increase the cost of treatment. Most protein products currently on the market require frequent injections, usually multiple times per week. This dosing regimen is painful, inconvenient for the patient, and may not provide the optimum therapeutic benefit. In the case of a chronic indication such as cancer or an immunodeficiency, treatment could last for years.

Thus, there is a strong need to develop protein delivery technologies that lower the costs of protein therapeutics to patients and healthcare providers. One solution to this problem is the development of methods to prolong the circulating half-lives of protein therapeutics in the body so that the proteins do not have to be injected frequently. This solution also satisfies the needs and desires of patients for protein therapeutics that are "user-friendly", i.e., protein therapeutics that do not require frequent injections.

Many bioactive peptides have been described, including glucagon, glucagon-like peptide-1 (GLP-1), GLP-2, Gastric inhibitory peptide (GIP), PYY, exendin, ghrelin, gastrin, amylin, and oxyntomoldulin. These peptides typically are 10-40 amino acids in length. Methods to develop longer acting forms of these peptides are desired.

In addition, larger proteins, such as interferon-gamma (IFN-γ) are of high interest as therapeutics. IFN-γ was first recognized over 35 years ago on the basis of its anti-viral activity (Wheelock, 1965). Over the years, a great deal of information has accumulated that validates IFN-γ's role in modulating nearly all phases of immune and inflammatory processes. IFN-γ belongs to a family of proteins related both structurally and by their ability to protect cells from viral infection. The interferon family has three main members, now designated interferon-alpha (IFN-α), interferon-beta (IFN-β), and interferon-gamma (IFN-γ). The latter, which is also known as immune or type II interferon, has several properties related to immunoregulation that makes it different from the other IFNs. For example, IFN-γ has a 10-fold lower specific anti-viral activity than either IFN-α or IFN-β. On the other hand IFN-γ is 100-10,000 times more active as an immune system modulator than are the other classes of interferon, having potent phagocyte-activating effects not seen with other interferon types (Pace et al., 1985).

IFN-γ is a 20-25 kDa glycoprotein that exists as a homodimer in solution. Recombinant IFN-γ has an elimination half-life in the bloodstream after intravenous (iv) administration of 25-35 min and is essentially undetectable after 4 hours depending on the dose. The subcutaneous (sc) route generally results in a somewhat extended half-life of 5-6 hours (see review by Younes and Amsden, 2002). The recommended dosing schedule for IFN-γ is a sc injection of 50 μg/m² three times weekly. Relevant to this invention is the fact that IFN-γ has a short elimination half-life, whether given iv or sc, and thus requires relatively frequent re-administration.

Several studies have demonstrated that continuous exposure to IFN-γ enhances the protein's potency. Researchers have investigated the benefits of continuous infusion of IFN-γ versus once daily intraperitoneal injections in *Leishmania donavani*-infected mice. Daily dosing of IFN-γ did induce anti-microbial resistance, but these effects were considerably enhanced by continuous administration of a comparable dose (47% reduction in liver parasite burden versus 9%) (Murray, 1990). In a similar study, mice were infected with *Mycobacterium tuberculosis*. Continuous delivery of IFN-γ via an external pump, prolonged survival longer than did daily intramuscular IFN-γ injections (12 vs. 4 days longer than controls) (Flynn et al., 1993). These studies suggest a superior therapeutic benefit from constant circulating levels of IFN-γ. Unfortunately, continuous infusion of IFN-γ is not practical for most patients. Therefore the need still exists for a long acting form of IFN-γ.

Covalent modification of proteins with polyethylene glycol (PEG) has proven to be a useful method to extend the circulating half-lives of proteins in the body (Abuchowski et al., 1984; Meyers et al., 1991; Keating et al., 1993). Several PEGylated proteins are approved for use in humans or are in human clinical trials (Harris et al., 2003). Covalent attachment of PEG to a protein increases the protein's effective size and reduces its rate of clearance from the body, presumably through interference with protein removal pathways, including kidney glomerular filtration, proteolytic degradation as well as active clearance via specific receptors.

Given the therapeutic value of long-acting forms of IFN-γ, as well as other therapeutic proteins and peptides, there is a continued need in the art to provide new variants of IFN-γ that have improved stability, higher potency, greater solubility, longer circulating half-lives for less frequent dosing, and reduced antigenicity as compared to the parent (native) protein. In addition, since expression of recombinant proteins containing free cysteine residues has been problematic due to reactivity of the free sulfhydryl at physiological conditions, there also remains a need in the art for improved, cost-effective methods for manufacturing (producing) such proteins that result in high yields of biologically active product.

SUMMARY OF THE INVENTION

One embodiment of the invention relates to a method for refolding an insoluble protein or peptide that lacks essential disulfides and that comprises at least one free cysteine residue, comprising the following steps: (a) causing a host cell to express a protein or peptide that lacks essential disulfides and that comprises at least one free cysteine residue in an insoluble or aggregated form; (b) lysing the host cell; (c) isolating the protein or peptide; (d) denaturing and reducing the protein or peptide in a solution comprising both a denaturing agent and a reducing agent, wherein said reducing agent does not form a mixed disulfide with the free cysteine in the protein or peptide, and wherein said reducing agent does not inactivate a thiol-reactive polyethylene glycol (PEG) or does not interfere with modification of the protein by a thiol-reactive PEG reagent; and (e) refolding the protein by reducing the concentrations of the denaturing agent and reducing agents in the solution of (d) to levels sufficient to allow the protein or peptide to renature into a soluble, biologically active form.

In one aspect, the step of lysing can be performed by chemical, enzymatic or physical means. In one aspect, the step of lysing comprises lysing the host cell in the presence of a denaturing agent. In another aspect, the step of lysing comprises lysing the host cell in the presence of a denaturing agent and the reducing agent used in step (d).

In one aspect of the method, the denaturing agent is selected from the group consisting of: urea, guanidine and N-lauroyl sarcosine.

In one aspect of the method, the reducing agent in step (d) is a reducing agent that does not contain a thiol moiety. In another aspect, the reducing agent in step (d) is a phosphine reductant. In one aspect, the reducing agent in step (d) is an alkyl phosphine. In one aspect, the alkyl phosphine can include, but is not limited to, a butyl phosphine, a hydroxypropyl phosphine, a cyanoethyl phosphine, and a carboxyethyl phosphine. In one aspect, the alkyl phosphine can include, but is not limited to: tri-n-butylphosphine (TBP), tris(hydroxypropyl)phosphine (THP), tris(2-cyanoethyl) phosphine (TCNP), and tris(2-carboxyethyl)phosphine (TCEP), or a combination thereof. In a preferred aspect, the alkyl phosphine is an ester of a carboxyethyl phosphine. In another preferred aspect, the reducing agent is Tris (2-carboxyethyl)phosphine-HCl (TCEP).

In one aspect of the method, step (e) occurs in the presence of sufficient reducing agent to prevent the protein from forming disulfide bonds. In one aspect, step (e) of refolding comprises refolding the protein in the presence of glycerol. In one aspect, step (e) of refolding comprises refolding the protein in the presence of an oxidizing agent selected from oxygen, iodine, hydrogen peroxide, dihydroascorbic acid, tetrathionate, or O-iodosobenzoate. In one aspect, step (e) of refolding comprises refolding the protein in the presence of a metal ion. Such a metal ion can include, but is not limited to, $Cu^{++}$ or $Co^{++}$.

The method of the invention can further include a step of isolating the refolded protein or peptide from other proteins and contaminants in the refold mixture. In one aspect, the protein is isolated from other contaminants in the refold mixture by column chromatography. For example, in one aspect, the column chromatography buffers can contain a reducing agent, wherein said reducing agent does not form a mixed disulfide with the free cysteine in the protein or peptide, and wherein said reducing agent does not inactivate a thiol-reactive polyethylene glycol (PEG) or does not interfere with modification of the protein by a thiol-reactive PEG reagent. In one aspect, the reducing agent used in the column is the same reducing agent used in step (d).

The method of the invention can also include a further step of exposing the protein or peptide to a cysteine-reactive moiety to obtain a cysteine-modified protein, wherein the cysteine-reactive moiety is attached to at least one added cysteine in said isolated protein or peptide. In one aspect, the step of exposing is conducted in the presence of a reducing agent. For example, in one aspect, the reducing agent is the same reducing agent used in step (d). Cysteine-reactive moieties can include, but are not limited to, a polyethylene glycol, a polyvinyl pyrolidone, a carbohydrate, a dextran, a peptide, a lipid and a polysaccharide. In a preferred embodiment, the cysteine-reactive moiety is a polyethylene glycol.

The proteins to be refolded using the method of the invention can include any protein or peptide that lacks essential disulfides and that comprises at least one free cysteine residue, including, but not limited to a cysteine variant of interferon-gamma (IFN-γ), a cysteine variant of interleukin-11, or a cysteine variant of growth hormone. In one aspect, the protein is a cysteine variant of IFN-γ, and the amino acid Q1 is deleted or substituted by a non-glutamine amino acid, and/or the amino acid D2 is deleted or substituted by a non-aspartic acid amino acid. Peptides that can be refolded using the method of the invention include, but are not limited to, a cysteine variant of a bioactive peptide selected from: glucagon, glucagon-like peptide-1 (GLP-1), GLP-2, Gastric inhibitory peptide (GIP), PYY, exendin, ghrelin, gastrin, amylin, and oxyntomodulin.

Another embodiment of the invention relates to a cysteine variant of interferon-gamma (IFN-γ) (SEQ ID NO:1) isolated from step (e) of the method of refolding of claim 1, wherein the cysteine variant of IFN-γ does not contain mixed disulfides.

One embodiment of the invention relates to a method for refolding an insoluble protein or peptide that lacks essential disulfides and that comprises at least one free cysteine residue, comprising the following steps: (a) causing a host cell to express a protein or peptide that lacks essential disulfides and that comprises at least one free cysteine residue in an insoluble or aggregated form; (b) lysing the host cell; (c) isolating the protein or peptide; (d) denaturing and reducing the protein or peptide in a solution comprising both a denaturing agent and a reducing agent; (e) refolding the protein by reducing the concentrations of the denaturing agent and reducing agents in the solution of (d) to levels sufficient to allow the protein or peptide to renature into a soluble, biologically active form; (f) isolating the protein from other contaminants in the refold mixture by column chromatography, wherein the column chromatography buffers contain a reducing agent, wherein said reducing agent does not form a mixed disulfide with the free cysteine in the protein or peptide, and wherein said reducing agent does not inactivate a thiol-reactive polyethylene glycol (PEG) or does not interfere with modification of the protein by a thiol-reactive PEG reagent. In one aspect, the reducing agent in step (f) is TCEP.

Yet another embodiment of the invention relates to a cysteine variant of interferon-gamma (IFN-γ) (SEQ ID NO:1), wherein a cysteine residue is substituted for at least one amino acid located in at least one region of IFN-gamma selected from the group consisting of: the E-F loop and the region following helix F. In one aspect, a cysteine residue is substituted for an amino acid selected from: V99, V100, T101, D102, L103, P122, A123, A124, K125, T126, G127, K128, R129, K130, R131, S132, Q133, M134, L135, F136, R137, G138, R139, R140, A141, S143, or Q143. In one aspect, the variant is modified with a cysteine reactive moiety, such as a polyethylene glycol. In one aspect, Q1 is deleted or substituted by a non-glutamine amino acid. In another aspect, D2 is deleted or substituted by a non-aspartic acid amino acid.

Another embodiment of the invention relates to a method for treating a disease treatable with IFN-gamma, comprising administering to said patient a therapeutically effective amount of a cysteine variant of IFN-gamma as described herein. Such a disease includes, but is not limited to, chronic granulomatous disease, severe malignant osteopetrosis, or cancer.

Yet another embodiment of the invention relates to a cysteine analog of glucagon-like peptide-1 (GLP-1) (SEQ ID NO:9), wherein a cysteine residue is added to the peptide either by substitution for a native amino acid in GLP-1 or by insertion preceding the first amino acid of GLP-1 or following the last amino acid of GLP-1. In one aspect, a cysteine residue is substituted for at least one amino acid selected from the group consisting of H1, A2, E3, G4, T5, F6, T7, S8, D9, V10, S11, S12, Y13, L13, E14, G15, Q16, A17, A18, K19, E20, F21, I22, A23, W24, L25, V26, K27, G28, R29, or G30. In another aspect, a cysteine residue is inserted preceding the first amino acid of GLP-1 or following the last amino acid of GLP-1.

Another embodiment of the invention relates to a cysteine analog of exendin (SEQ ID NO:11), wherein a cysteine residue is added to the peptide either by substitution for a native amino acid in exendin or by insertion preceding the first amino acid of exendin or following the last amino acid of exendin. In one aspect, a cysteine residue is substituted for an amino acid selected from the group consisting of H1, G2, E3, G4, T5, F6, T7, S8, D9, L10, S11, K12, Q13, M14, E15, E16, E17, A18, V19, R20, L21, F22, I23, E24, W25, L26, K27, N28, G29, G30, P31, S32, S33, G34, A35, P36, P37, P38 and S39. In another aspect, a cysteine residue is inserted preceding the first amino acid of exendin or following the last amino acid of exendin.

Another embodiment of the invention relates to a cysteine analog of amylin (SEQ ID NO:17), wherein a cysteine residue is added to the peptide either by substitution for a native amino acid in amylin or by insertion preceding the first amino acid of amylin or following the last amino acid of amylin. In one aspect, a cysteine residue is substituted for an amino acid selected from the group consisting of K1, N3, T4, A5, T6, A8, T9, Q10, R11, L12, A13, N14, F15, L16, V17, H18, S19, S20, N21, N22, F23, G24, A25, I26, L27, S28, S29, T30, N31, V32, G33, S34, N35, T36, and Y37. In another aspect, a cysteine residue is inserted preceding the first amino acid of amylin or following the last amino acid of amylin.

Yet another embodiment of the invention relates to a cysteine analog of glucagon (SEQ ID NO:8), wherein a cysteine residue is added to the peptide either by substitution for a native amino acid in glucagon or by insertion preceding the first amino acid of glucagon or following the last amino acid of glucagon. In one aspect, a cysteine residue is substituted for an amino acid selected from the group consisting of H1, S2, Q3, G4, T5, F6, T7, S8, D9, Y10, S11, K12, Y13, L14, D15, S16, R17, R18, A19, Q20, D21, F22, V23, Q24, W25, L26, M27, N28, and T29. In another aspect, a cysteine residue is inserted preceding the first amino acid of glucagon or following the last amino acid of glucagon.

Another embodiment of the invention relates to a cysteine analog of GLP-2 (SEQ ID NO:10), wherein a cysteine residue is added to the peptide either by substitution for a native amino acid in GLP-2 or by insertion preceding the first amino acid of GLP-2 or following the last amino acid of GLP-2. In one aspect, a cysteine residue is substituted for an amino acid selected from the group consisting of H1, A2, D3, G4, S5, F6, S7, D8, E9, M10, N11, T12, I13, L14, D15, N16, L17, A18, A19, R20, D21, F22, I23, N24, W25, L26, I27, Q28, T29, K30, I31, T32, and D33. In another aspect, a cysteine residue is inserted preceding the first amino acid of GLP-2 or following the last amino acid of GLP-2.

Yet another embodiment of the invention relates to a cysteine analog of Peptide YY (PYY) (SEQ ID NO:12), wherein a cysteine residue is added to the peptide either by substitution for a native amino acid in PYY or by insertion preceding the first amino acid of PYY or following the last amino acid of PYY. In one aspect, a cysteine residue is substituted for an amino acid selected from the group consisting of Y1, P2, I3, K4, P5, E6, A7, P8, G9, E10, D11, A12, S13, P14, E15, E16, L17, N18, R19, Y20, Y21, A22, S23, L24, R25, H26, Y27, L28, N29, L30, V31, T32, R33, Q34, R35, and Y36. In another aspect, a cysteine residue is inserted preceding the first amino acid of PYY or following the last amino acid of PYY.

Another embodiment of the invention relates to a cysteine analog of ghrelin (SEQ ID NO:13), wherein a cysteine residue is added to the peptide either by substitution for a native amino acid in ghrelin or by insertion preceding the first amino acid of ghrelin or following the last amino acid of ghrelin. In one aspect, a cysteine residue is substituted for an amino acid selected from the group consisting of G1, S2, S3, F4, L5, S6, P7, E8, H9, Q10, R11, V12, Q13, Q14, R15, K16, E17, S18, K19, K20, P21, P22, A23, K24, L25, Q26, P27, and R28. In another aspect, a cysteine residue is inserted preceding the first amino acid of ghrelin or following the last amino acid of ghrelin. In one aspect, S3 of ghrelin is acetylated.

Another embodiment of the invention relates to cysteine analog of oxyntomodulin (SEQ ID NO:14), wherein a cysteine residue is added to the peptide either by substitution for a native amino acid in oxyntomodulin or by insertion preceding the first amino acid of oxyntomodulin or following the last amino acid of oxyntomodulin. In one aspect, a cysteine residue is substituted for an amino acid selected from the group consisting of H1, S2, Q3, G4, T5, F6, T7, S8, D9, Y10, S11, K12, Y13, L14, D15, S16, R17, R18, A19, Q20, D21, F22, V23, Q24, W25, L26, M27, D28, T29, K30, R31, N32, K33, N34, N35, I36, and A37. In another aspect, a cysteine residue is inserted preceding the first amino acid of oxyntomodulin or following the last amino acid of oxyntomodulin.

Another embodiment of the invention relates to a cysteine analog of GIP (SEQ ID NO:16), wherein a cysteine residue is added to the peptide either by substitution for a native amino acid in GIP or by insertion preceding the first amino acid of GIP or following the last amino acid of GIP. In one aspect, a cysteine residue is substituted for an amino acid selected from the group consisting of Y1, A2, E3, G4, T5, F6, I7, S8, D9, Y10, S11, I12, A13, M14, D15, K16, I17, H18, Q19, Q20, D21, F22, V23, N24, W25, L26, L27, A28, Q29, K30, G31, K32, K33, N34, D35, W36, K37, H38, N39, I40, T41 and Q42. In another aspect, a cysteine residue is inserted preceding the first amino acid of GIP or following the last amino acid of GIP.

In one aspect of any of the above-identified embodiments related to cysteine analogs, the added cysteine residue is modified with a cysteine-reactive moiety. For example, the cysteine-reactive moiety can include, but is not limited to, a polyethylene glycol.

Another embodiment of the invention relates to a lysine analog of amylin (SEQ ID NO:17), wherein a lysine residue is added to the peptide either by substitution for a native amino acid in amylin or by insertion preceding the first amino acid of amylin or following the last amino acid of amylin. In one aspect, a lysine residue is substituted for an amino acid selected from the group consisting of N3, T4, A5, T6, A8, T9, Q10, R11, L12, A13, N14, F15, L16, V17, H18, S19, S20, N21, N22, F23, G24, A25, I26, L27, S28, S29, T30, N31, V32, G33, S34, N35, T36, and Y37. In another aspect, a lysine residue is inserted preceding the first amino acid of amylin or following the last amino acid of amylin. In one aspect, K1 is changed to a non-lysine amino acid.

Yet another embodiment of the invention relates to a lysine analog of glucagon (SEQ ID NO:8), wherein a lysine residue is added to the peptide either by substitution for a native amino acid in glucagon or by insertion preceding the first amino acid of glucagon or following the last amino acid of glucagon. In one aspect, a lysine residue is substituted for an amino acid selected from the group consisting of H1, S2, Q3, G4, T5, F6, T7, S8, D9, Y10, S11, Y13, L14, D15, S16, R17, R18, A19, Q20, D21, F22, V23, Q24, W25, L26, M27, N28, and T29. In another aspect, a lysine residue is inserted preceding the first amino acid of glucagon or following the last amino acid of glucagon. In one aspect, K12 is changed to a non-lysine amino acid.

Another embodiment of the invention relates to a lysine analog of glucagon-like peptide-1 (GLP-1) (SEQ ID NO:9), wherein a lysine residue is added to the peptide either by substitution for a native amino acid in GLP-1 or by insertion preceding the first amino acid of GLP-1 or following the last amino acid of GLP-1. In one aspect, a lysine residue is substituted for at least one amino acid selected from the group consisting of H1, A2, E3, G4, T5, F6, T7, S8, D9, V10, S11, S12, Y13, L13, E14, G15, Q16, A17, A18, E20, F21, I22, A23, W24, L25, V26, G28, R29, and G30. In one aspect, a lysine residue is inserted preceding the first amino acid of GLP-1 or following the last amino acid of GLP-1. In another aspect, K20 is changed to a non-lysine amino acid. In one aspect, K28 is changed to a non-lysine amino acid. In another aspect, K20 and K28 are changed to non-lysine amino acids, or K19 and K27 are changed to non-lysine amino acids.

Yet another embodiment of the invention relates to a lysine analog of GLP-2 (SEQ ID NO:10), wherein a lysine residue is added to the peptide either by substitution for a native amino acid in GLP-2 or by insertion preceding the first amino acid of GLP-2 or following the last amino acid of GLP-2. In one aspect, a lysine residue is substituted for an amino acid selected from the group consisting of H1, A2, D3, G4, S5, F6, S7, D8, E9, M10, N11, T12, I13, L14, D15, N16, L17, A18, A19, R20, D21, F22, I23, N24, W25, L26, I27, Q28, T29, I31, T32, and D33. In one aspect, a lysine residue is inserted preceding the first amino acid of GLP-2 or following the last amino acid of GLP-2. In another aspect, K30 is changed to a non-lysine amino acid.

Another embodiment of the invention relates to a lysine analog of exendin (SEQ ID NO:11), wherein a lysine residue is added to the peptide either by substitution for a native amino acid in exendin or by insertion preceding the first amino acid of exendin or following the last amino acid of exendin. In one aspect, a lysine residue is substituted for an amino acid selected from the group consisting of H1, G2, E3, G4, T5, F6, T7, S8, D9, L10, S11, Q13, M14, E15, E16, E17, A18, V19, R20, L21, F22, I23, E24, W25, L26, N28, G29, G30, P31, S32, S33, G34, A35, P36, P37, and S38. In another aspect, a lysine residue is inserted preceding the first amino acid of exendin or following the last amino acid of exendin. In one aspect, K12 is changed to a non-lysine amino acid. In another aspect, K27 is changed to a non-lysine amino acid. In yet another aspect, K12 and K27 are changed to non-lysine amino acids.

Another embodiment of the invention relates to a lysine analog of oxyntomodulin (SEQ ID NO:14), wherein a lysine residue is added to the peptide either by substitution for a native amino acid in oxyntomodulin or by insertion preceding the first amino acid of oxyntomodulin or following the last amino acid of oxyntomodulin. In one aspect, a lysine residue is substituted for an amino acid selected from the group consisting of H1, S2, Q3, G4, T5, F6, T7, S8, D9, Y10, S11, Y13, L14, D15, S16, R17, R18, A19, Q20, D21, F22, V23, Q24, W25, L26, M27, D28, T29, R31, N32, N34, N35, I36, and A37. In one aspect, a lysine residue is inserted preceding the first amino acid of oxyntomodulin or following the last amino acid of oxyntomodulin. In one aspect, an amino acid selected from K12, K30 and K33 is changed to a non-lysine amino acid. In one aspect, two or more lysine residues selected from the group consisting of K12, K30 and K33 are changed to non-lysine amino acids. In one aspect, K12, K30 and K33 are changed to non-lysine amino acids.

Another embodiment of the invention relates to a lysine analog of ghrelin (SEQ ID NO:13), wherein a lysine residue is added to the peptide either by substitution for a native amino acid in ghrelin or by insertion preceding the first amino acid of ghrelin or following the last amino acid of ghrelin. In one aspect, a lysine residue is substituted for an amino acid selected from the group consisting of G1, S2, S3, F4, L5, S6, P7, E8, H9, Q10, R11, V12, Q13, Q14, R15, E17, S18, P21, P22, A23, L25, Q26, P27, and R28. In one aspect, a lysine residue is inserted preceding the first amino acid of ghrelin or following the last amino acid of ghrelin. In one aspect, S3 of ghrelin is acetylated. In another aspect, an amino acid selected from K16, K19, K20, and K24 is changed to a non-lysine amino acid. In one aspect, two or more lysine residues selected from the group consisting of K16, K19, K20 and K24 are changed to non-lysine amino acids. In another aspect, K12, K19, K20 and K24 are changed to non-lysine amino acids.

Yet another embodiment of the invention relates to a lysine analog of Peptide YY (PYY) (SEQ ID NO:12), wherein a lysine residue is added to the peptide either by substitution for a native amino acid in PYY or by insertion preceding the first amino acid of PYY or following the last amino acid of PYY. In one aspect, a lysine residue is substituted for an amino acid selected from the group consisting of Y1, P2, I3, P5, E6, A7, P8, G9, E10, D11, A12, S13, P14, E15, E16, L17, N18, R19, Y20, Y21, A22, S23, L24, R25, H26, Y27, L28, N29, L30, V31, T32, R33, Q34, R35, and Y36. In another aspect, a lysine residue is inserted preceding the first amino acid of PYY or following the last amino acid of PYY. In another aspect, K4 is changed to a non-lysine amino acid.

Another embodiment of the invention relates to a lysine analog of GIP (SEQ ID NO:16), wherein a lysine residue is added to the peptide either by substitution for a native amino acid in GIP or by insertion preceding the first amino acid of GIP or following the last amino acid of GIP. In one aspect, a lysine residue is substituted for an amino acid selected from the group consisting of Y1, A2, E3, G4, T5, F6, I7, S8, D9, Y10, S11, I12, A13, M14, D15, I17, H18, Q19, Q20, D21, F22, V23, N24, W25, L26, L27, A28, Q29, G31, N34, D35, W36, H38, N39, I40, T41 and Q42. In one aspect, a lysine residue is inserted preceding the first amino acid of GIP or following the last amino acid of GIP. In another aspect, an amino acid selected from K16, K30, K32, K33, and K37 is changed to a non-lysine amino acid. In one aspect, two or more lysine residues selected from the group consisting of K16, K30, K32, K33 and K37 are changed to non-lysine amino acids. In another aspect, K16, K30, K32, K33 and K37 are changed to non-lysine amino acids.

In any of the above-embodiments related to lysine analogs, in one aspect, the added lysine residue is modified with an amine-reactive moiety. For example, such an amine-reactive moiety can include, but is not limited to, a polyethylene glycol.

DETAILED DESCRIPTION OF THE INVENTION

One embodiment of the invention describes novel polymer IFN-γ conjugates that have been created by the chemical coupling of polymers such as polyethylene glycol moieties to IFN-γ. Based on the present inventors' work, these novel IFN-γ-based protein polymer conjugates will have improved stability, higher potency, greater solubility, longer circulating half-lives for less frequent dosing, and reduced antigenicity as compared to the parent (native or wild-type) protein. Methods of making and using the variants are encompassed by the invention.

Additional embodiments of the invention related to novel analogs of bioactive peptides that may be used to create longer acting versions of the peptides. The longer-acting peptides are useful because they can be administered at lower doses and less frequently than the unmodified peptides. Such bioactive peptides include, but are not limited to, glucagon, glucagon-like peptide-1 (GLP-1), GLP-2, Gastric inhibitory peptide (GIP), PYY, exendin, ghrelin, gastrin, amylin, and oxyntomoldulin. Methods of making and using such peptides are also encompassed by the invention.

In one embodiment, the invention provides a novel method for producing, and particularly, refolding, the novel IFN-γ-based protein polymer conjugates of the invention, which can be extended to the production of any protein or peptide that does not contain essential disulfides (i.e. disulfides that are essential for the proper folding and/or biological activity of the protein), and that contains at least one free cysteine residue.

Various aspects of the present invention are described in detail below, although particular examples are not intended to limit the scope of the present invention.

Method of Producing Proteins and Peptides According to the Invention

One embodiment of the present invention relates to a novel method to refold a protein or a peptide that does not contain essential disulfides and that comprises at least one free cysteine. More particularly, cysteine residues in most proteins participate in disulfide bonds and are not available for derivatization without significant loss of bioactivity. These disulfide bonds are referred to herein as "essential" disulfides, in that they are required for the proper folding and/or the biological activity of the protein. However, some proteins and peptides contain "non-essential" disulfides, i.e., disulfide bonds that are not required for the proper folding of the protein and/or are not required for biological activity of the protein. In addition, some proteins and peptides contain no native cysteine residues and thus contain no native disulfide bonds. In addition, some proteins naturally contain, or can be modified to contain, one or more free cysteine residues that do not participate in disulfides. For example, through in vitro site-directed mutagenesis techniques, additional cysteine residues can be introduced at a specified site on a protein or peptide, e.g., by substitution or insertion. Any free cysteine in a protein or peptide, including a free cysteine that occurs in the native (wild-type) protein, a free cysteine that is created by deleting or substituting a non-cysteine residue for one cysteine in a non-essential disulfide, or a newly added "free" cysteine (e.g., as a result of substitution of a cysteine for a non-cysteine residue or the insertion of a cysteine into a protein or peptide), can then serve as the site for the specific conjugation with a thiol-reactive moiety (e.g., thiol-reactive polyethylene glycol). The present invention provides a novel method of efficiently and effectively producing such proteins and peptides in a cost-effective manner.

Accordingly, the present invention encompasses a wide variety of recombinant proteins, and cysteine variants of these proteins. Examples of proteins that can be refolded using the method of the invention include, but are not limited to, cysteine variants of: interferon-gamma (IFN-γ), interleukin-11 (IL-11), growth hormone, glucagon, glucagon-like peptide-1 (GLP-1), GLP-2, Gastric inhibitory peptide (GIP), PYY, exendin, ghrelin, gastrin, amylin, oxyntomoldulin, and other proteins and peptides that do not contain native cysteine residues. Any protein or peptide that has at least one free cysteine (native or added by modification of the protein or peptide) and does not otherwise contain essential disulfides can be refolded using this method. Such proteins include proteins that lack essential disulfides, but contain at least one free cysteine that is not involved in a disulfide bond; proteins that lack essential disulfides, but contain non-essential disulfides, where the protein has been modified to delete one of the cysteines in the non-essential disulfide pair (leaving one free cysteine); or proteins or peptides in which a free cysteine has been added by inserting it before the first amino acid of the protein or after the last amino acid of the protein, or by inserting it between two of the native amino acid residues, or by substituting a cysteine residue for a non-cysteine residue in the protein.

The method of the invention generally includes the steps of: (a) causing a host cell to express a protein or peptide that lacks essential disulfides and that comprises at least one free cysteine residue in an insoluble or aggregated form; (b) lysing the host cell; (c) isolating the protein or peptide; (d) denaturing and reducing the protein or peptide in a solution comprising both a denaturing agent and a reducing agent, wherein said reducing agent does not form a mixed disulfide with the free cysteine in the protein or peptide, and wherein said reducing agent does not inactivate a thiol-reactive polyethylene glycol (PEG) or does not interfere with modification of the protein by a thiol-reactive PEG reagent; and (e) refolding the protein by reducing the concentrations of the denaturing agent and reducing agents in the solution of (d) to levels sufficient to allow the protein or peptide to renature into a soluble, biologically active form. If the user of the method is provided with an isolated, insoluble or aggregated protein or peptide that lacks essential disulfides and that comprises at least one free cysteine residue, then the method can also begin with step (d), since steps (a) through (c) may have been performed independently. In another embodiment, the cell can be lysed directly into the solution comprising the denaturing agent and the reducing agent described above, rather than isolating the protein first as in step (c). Optionally, in any of the above-methods, the refolded, soluble protein can be isolated from other proteins in the refold mixture. In a preferred embodiment, the refolded protein is isolated from other proteins in the refold mixture by column chromatography. Preferably, the column chromatography buffers used to isolate the refolded protein contain a reducing agent that does not inactivate a thiol-reactive PEG reagent, or does not interfere with modification of the protein by a thiol-reactive PEG reagent. In another embodiment, a reducing agent that does inactivate a thiol-reactive PEG can be used to reduce the protein in step (d), but the protein is purified subsequently using column buffers that contain a reducing agent that does not inactivate a thiol-reactive PEG reagent, or does not interfere with modification of the protein by a thiol-reactive PEG reagent.

One advantage of the method of the invention, however, is that the proteins do not necessarily have to be purified away from the reducing agent used in step (d) prior to further modification with a thiol-reactive polyethylene glycol, because the reducing agent does not inactivate PEG or interfere with modification of the protein by a thiol-reactive PEG reagent. In methods described prior to the invention, a protein refolded using other thiol-reactive reducing agents (e.g., DTT, cysteine) that do inactivate thiol-reactive PEGs or interfere with modification of a protein with a thiol-reactive PEG, would have to be dialyzed to remove the reducing agent prior to PEGylation. Therefore, PEGylation of proteins refolded by the method of the invention is more efficient and removes a step in the PEGylation process (and thus is more cost effective). In addition, the use of a reducing agent specified in the present method (does not form a mixed disulfide with the free cysteine in the protein or peptide, and does not inactivate a thiol-reactive polyethylene glycol (PEG) or interfere with modification of a protein with a thiol-reactive PEG), the resulting product is qualitatively better than with certain reducing agents (e.g., cysteine), because the resulting refolded protein is mostly non-disulfide bonded and monomeric (or homodimeric in the case of interferon gamma), whereas other reducing agents can produce more disulfide-linked dimers, tetramers, or multimers, or undesired disulfide-linked aggregates. The monomeric form, or in the case of certain proteins (e.g., interferon gamma), a homodimeric form, is the preferred commercial product, and so methods that enhance the ability to produce and recover these preferred forms is of great value.

Accordingly, the use of a reducing agent such as the exemplary TCEP in the method of the invention both improves the quality of the refolded product (i.e., more non-disulfide bonded product) and allows efficient PEGylation of the refolded product because the agent does not have to be removed prior to PEGylation. Indeed, if desired, such a reducing agent could be added as a reducing agent in the PEGylation process or purification steps prior to PEGylation to facilitate the PEGylation reaction.

The reducing agent for use in the denaturing and reducing step (d) (and in some embodiments, in subsequent steps) is preferably a phosphine reductant and, more preferably, an alkyl phosphine. Exemplary alkyl phosphines for use in the methods of the present invention include, but are not limited to, alkyl phosphines such as tri-n-butylphosphine (TBP), hydroxypropyl phosphines such as tris(hydroxypropyl) phosphine (THP), cyanoethyl phosphines such as tris(2-cyanoethyl)phosphine (TCNP), carboxyethyl phosphines such as tris(2-carboxyethyl)phosphine (TCEP) and any combination of these reductants. Additionally, esters of the carboxyethyl phosphines such as monomethyl-, dimethyl- or trimethyl-esters of tris(2-carboxyethyl)phosphine (TCEP) or combinations thereof may be used in the denaturing and reducing reactions of the inventive processes. The selection of the appropriate phosphine reductant(s) for use in the methods of the present invention will depend upon the chemical characteristics of the isolated protein or peptide to be refolded using the methodology described herein. For example, a protein isolated and stabilized at an acidic pH less than about 5.5 having one or more free cysteine residues may require a phosphine reducing agent having a stronger reducing reactivity at a lower pH, such as the trimethylester of TCEP, while retaining the biochemical characteristics of acting in concert with a denaturing agent in a single denaturing and reducing step, and limited or absent inhibitory effect on the PEGylation reaction, such that it does not need to be removed by dialysis or other methods prior to PEGylation. Similarly, a protein isolated and stabilized at a more basic pH of about 8.0 having one or more free cysteine residues may require a phosphine reducing agent having a stronger reducing reactivity at a higher pH, such as TCEP. Preferably, the reducing agent for use in the protein denaturing and reducing reactions of the present invention is an alkyl phosphine, more preferably the reducing agent is an ester derivative of TCEP, and most preferably the reducing agent is TCEP.

In another embodiment, the reducing agent for use in the denaturing and reducing steps, and/or in subsequent reducing steps of the method of the invention, is a reducing agent that does not contain a sulfur moiety.

As identified above, the first step in the method of the invention is to cause a host cell to express a protein having a free cysteine residue in an insoluble or aggregated form. Suitable host cells can be prokaryotic or eukaryotic. Examples of appropriate host cells that can be used to express recombinant proteins include bacteria, yeast, insect and mammalian cells. Bacteria cells are particularly useful, especially *E. coli*. Methods of causing a host cell to express a protein are well known in the art and examples are provided herein.

As used herein, the term "protein having a free cysteine residue" means any natural or recombinant protein or peptide that contains 2N+1 cysteine residues, where N can be 0 or any integer, and any natural or recombinant protein or peptide that contain 2N cysteines, where two or more of the cysteines do not normally participate in a disulfide bond. Thus, the methods of the present invention are useful in enhancing the expression, recovery and purification of any protein or peptide having a free cysteine, particularly cysteine added variant recombinant proteins (referred to herein as "cysteine muteins" or "cysteine variants") having one or more free cysteines. As previously discussed, the invention is primarily intended to be used for proteins that do not contain an essential disulfide (two cysteines that form a disulfide bond that is essential to the ability of the protein to fold and/or have biological activity). Although the expression, recovery and purification of a natural protein having a free cysteine expressed by its natural host cell can be enhanced by the methods of the present invention, the description herein predominantly refers to recombinant proteins for illustrative purposes only. In addition, the proteins can be derived from any animal species including human, companion animals and farm animals. The proteins also can be derived from plant species or microbes.

In one step of the method, after the protein is expressed by the cell, the host cell is lysed. Cell lysis can occur prior to, or coincident with, the solubilization procedures described herein. Cell lysis can be accomplished by, for example, mechanical sheer such as a French pressure cell, enzymatic digestion, sonication, homogenization, glass bead vortexing, detergent treatment, organic solvents, freeze thaw, grinding with alumina or sand, treatment with a denaturing agent as defined below, and the like (Bollag et al., 1996). Optionally, the cells can be lysed in the presence of a denaturing agent and a disulfide reducing agent, preferably those in the solution used to solubilize the protein. Optionally, insoluble or aggregated material can be separated from soluble proteins prior to the solubilization step by various methods such as centrifugation, filtration (including ultrafiltration), precipitation, flocculation, or settling.

Next the insoluble or aggregated material (or whole cells without prior lysis) is rendered soluble or monomeric by exposing the insoluble or aggregated material (or whole cells without prior lysis) to a solution comprising both a denaturing agent and a disulfide reducing agent that does not form a mixed disulfide with the free cysteine in the protein or peptide, and does not inactivate a thiol-reactive polyethylene glycol (PEG).

Useful denaturing agents include urea, guandine, arginine, sodium thiocyanate, extremes in pH (dilute acids or bases), detergents (SDS, sarkosyl), salts (chlorides, nitrates, thiocyanates, cetylmethylammonium salts, trichloroacetates), chemical derivatization (sulfitolysis, reaction with citraconic anhydride), solvents (2-amino-2-methyl-1-propanol or other alcohols, DMSO, DMF) or strong anion exchange resins such as Q-Sepharose. Useful concentrations of urea are 1-8 M, with 5-8 M being preferred concentrations. Useful concentrations of guanidine are 1-8 M, with 4-8 M being preferred concentrations.

Useful disulfide reducing agents are any reducing agents that do not form a mixed disulfide with the free cysteine in the protein or peptide, and that do not inactivate a thiol-reactive polyethylene glycol (PEG), or interfere with modification of the protein with a thiol-reactive PEG. In one embodiment, such a reducing agent is a phosphine reductant and, more preferably, an alkyl phosphine. In one embodiment, an alkyl phosphine includes, but is not limited to, an alkyl phosphine such as tri-n-butylphosphine (TBP), a hydroxypropyl phosphine such as tris(hydroxypropyl)phosphine (THP), a cyanoethyl phosphine such as tris(2-cyanoethyl)phosphine (TCNP), a carboxyethyl phosphine such as tris(2-carboxyethyl)phosphine (TCEP) and any combination of these reductants. In one embodiment, the reducing agent is an ester of the carboxyethyl phosphines such as monomethyl-, dimethyl- or trimethyl-esters of tris(2-carboxyethyl)phosphine (TCEP) or combinations thereof. In one preferred embodiment, the reducing agent is an ester derivative of TCEP, and most preferably the reducing agent is TCEP. In one embodiment, the reducing agent is a reducing agent that does not contain a sulfur moiety.

These reducing agents can be used in the range of 0.5 to 200 mM, with 1-50 mM being preferred concentrations. Notably, it is not necessary to use a cysteine blocking agent in the method of the invention, because the method is used to refold proteins that do not contain (lack) essential disulfides, and so there is no need to block the free cysteines in the protein. Accordingly, in one aspect, the reducing agent is not a cysteine blocking agent. Preferably, the pH of the denaturation/reduction mixture is between pH 6 and pH 10.

The next step in the method of the invention is to refold the protein to obtain the protein's native conformation so that it can be further modified in biologically active form by a polymer, such as polyethylene glycol. Refolding is achieved by reducing the concentrations of the denaturing agent and reducing agent to levels sufficient to allow the protein to renature into a soluble, biologically active form. This can be achieved through dialysis, dilution, gel filtration, precipitation of the protein, or by immobilization on a resin followed by buffer washes. Preferably, a reagent or combination of reagents are chosen that result in refolding of the protein, while maintaining the protein in a reduced state so that the free cysteine(s) in the protein can be derivatized. Optionally, the reducing agent used in the refold step can be added to the dialysis buffer to keep the protein reduced during the renaturation process. Useful concentrations of the reducing agent in the dialysis buffer are 1 µM to 100 mM, with 0.1 mM to 10 mM being a preferred concentration and 1 mM being the most preferred concentration. Optionally, a metal ion such as copper ($Cu^{++}$) or cobalt ($Co^{++}$) can be added to the refold mixture to promote protein oxidation. Useful concentrations of metal ions in the refold mixture are 1 µM to 1 mM, with 40 µM being a preferred concentration. Preferably, the pH of the refold mixture is between pH 6 and pH 10.

Optionally, the refolded, soluble protein containing a free cysteine residue is recovered and isolated from other proteins in the soluble fraction of the refold mixture. Such recovery and purification methods are known or readily determined by those skilled in the art, including, for example, centrifugation, filtration, dialysis, chromatography, including size exclusion, ion-exchange, hydrophobic interaction and affinity chromatography procedures and the like. A suitable method for the recovery and purification of a desired protein will depend, in part, on the properties of the protein and the intended use. In a preferred embodiment the refolded protein is isolated from other proteins in the refold mixture by column chromatography. Preferably, the column chromatography buffers used to isolate the refolded protein contain a reducing agent that does not inactivate a thiol-reactive PEG reagent, or does not interfere with modification of the protein by a thiol-reactive PEG reagent. Useful concentrations of the reducing agent in the column chromatography buffers are 1 µM to 100 mM, with 0.1 mM to 10 mM being a preferred concentration and 1 mM being the most preferred concentration. If a reducing agent that does inactivate a thiol-reactive PEG is used to reduce the protein in step (d) above, the protein may be isolated from other proteins in the refold mixture using column chromatography buffers that contain a reducing agent that does not inactivate a thiol-reactive PEG reagent, or does not interfere with modification of the protein by a thiol-reactive PEG reagent.

The purified proteins obtained according to these methods can be further processed if desired, and indeed, the method of the invention is particularly useful for subsequent modification of the protein or peptide at the free cysteine residue with various cysteine-reactive moieties. For example, the proteins can be PEGylated at the free cysteine residue with various cysteine-reactive PEG reagents, and subsequently purified as monoPEGylated proteins. The term "monoPEGylated" is defined to mean a protein modified by covalent attachment of a single PEG molecule to the protein. Any method known to those skilled in the art can be used to purify the PEGylated protein from unmodified protein and unreacted PEG reagents, including, for example, the methods described in the Examples below, and in PCT/US98/14497 and PCT/US00/00931. Examples of other useful cysteine-reactive moieties are cysteine-reactive dextrans, cysteine-reactive carbohydrates and cysteine-reactive poly (N-vinylpyrrolidone)s.

One exemplary method of refolding a protein according to the present invention is described in detail in Example 3, wherein the reducing agent is TCEP. This example is for purposes of illustration only, and the invention is not limited to the details presented in this example.

The present invention further relates to purified, monoPEGylated or PEGylated protein variants produced by the methods disclosed herein that are not only biologically active, but also retain high specific activity in protein-dependent mammalian cell proliferation assays.

PEG Conjugation of Proteins According to the Invention

PEGs are commercially available in several sizes (2-40 kDa) and shapes (linear and branched), allowing the circulating half-lives of PEG-modified proteins to be tailored for individual indications through the use of different PEGs. PEGylation increases a protein's effective molecular weight more than would be expected based on the molecular weight of the PEG moiety due to the water of hydration associated with the PEG group. For example, attachment of a single 5 kDa PEG to a 36 kDa protein increases the effective molecular weight of the complex to greater than 100 kDa, as measured by size-exclusion chromatography (Fee, 2003). When administered by subcutaneous injection, PEGylated proteins are slowly absorbed from the injection site, thus avoiding the serum "spikes" seen after subcutaneous injection of an unmodified protein. This "controlled release" of the PEGylated protein results in a more constant serum level, thus prolonging or increasing the drug's pharmacologic activity while minimizing the side effects typically seen with fluctuations in the drug concentrations. Other documented in vivo benefits of PEG modification include an increase in protein solubility, enhanced stability (possibly due to protection from proteases) and a decrease in immunogenicity (Keating et al., 1993).

A PEG moiety can be attached to the N-terminal amino acid, a cysteine residue (either native or non-native), lysines (either native or non-native) or other reactive native or non-native amino acids in the protein's primary sequence. A non-native amino acid is defined as an amino acid that is not normally located at that position in the protein, an amino acid analog that is not commonly seen in native proteins, or an amino acid or amino acid analog that has been chemically modified to allow conjugation with a polymer such as polyethylene glycol. Although specific examples are provided herein with respect to the PEGylation of IFN-γ, it is to be understood that any protein or peptide having a free cysteine and that is produced by the method of the invention can be PEGylated using the methods described below.

Amine Reactive PEG Reagents for Modification of IFN-γ

The most common route for PEG conjugation of proteins is to use a PEG with a functional group that reacts with lysines and/or the N-terminal amino acid group. The literature describes more than a dozen such procedures (see reviews by Hooftman et al., 1996; Delgato et al., 1992; and Zalipsky, 1995). Examples of amine-reactive PEGs include PEG dichlorotriazine, PEG tresylate, PEG succinimidyl carbonate, PEG benzotriazole carbonate, PEG p-nitrophenyl carbonate, PEG carbonylimidazole, PEG succinimidyl succinate, PEG propionaldehyde, PEG acetaldehyde, and PEG hydroxysuccinimide.

Dimeric IFN-γ has 42 potential sites (two N-termini and 40 lysines) for conjugation with an amine reactive PEG. Multiple attachments may occur if the protein is exposed to an excess amount of PEGylation reagent. Preferably, the IFN-γ PEG conjugate would have 1-5 PEGs attached to the dimeric protein, more preferred would be 1-3 attachments, and most preferred 1-2 attachments. Conditions can be adjusted to limit the number of attachments or the site of attachments. The number of attachments can be titrated by varying the molar ratios of the PEG:Protein. Preferred ratios can be determined experimentally. A second method for varying the number of attachments is by modifying the reaction conditions. For example, the coupling can be preferentially directed to the alpha-terminus of a protein chain by performing the reaction at a pH lower than 7 and preferably below 6.5. Above pH 8, the epsilon-NH3 groups found on the lysines will be most reactive. (Morpurgo and Veronese, 2004). A third approach to controlling the number or location of the PEG conjugates is to conduct the PEGylation in the presence of a substrate, reversible inhibitor or binding protein so that the active site or receptor binding site is protected during coupling. A fourth approach to controlling the number of attachments involves using a larger PEG. For example, when interferon-alpha is modified with a small linear polymer, up to 11 positional isomers are present in the final mixture. When interferon-alpha is modified with a larger 40 kDa branched PEG, only four main positional isomers are present in the mono-PEGylated protein (Monkarsh et al., 1997, Foser et al. 2003, Baillon et al. 2003). A fifth method to control the number of attached PEGs is to use column chromatography procedures (ion exchange, size exclusion or hydrophobic interaction) to purify a IFN-γ conjugate containing the desired number of PEG molecules from a more complex IFN-γ-PEG mixture. Amine PEGylation of IFN-γ has been described by Kita et al. (1990). Amino acids 1 and lysine 129 or lysine 131 were modified by amine-reactive PEGs.

PEG-Protein Conjugates Using Cysteine-Reactive PEGs

A second method for PEGylating proteins covalently attaches PEG to cysteine residues using thiol-reactive PEGs. A number of highly specific, thiol-reactive PEGs with different reactive groups (e.g., PEG-ortho-pyridyl-disulfide, PEG-maleimide, PEG-vinylsulfone and PEG-iodoacetamide), different size PEGs (2-40 kDa), different shaped PEGs (linear or branched) and different end group (hydroxyl, carboxylic acid, methoxy or other alkoxy group) are commercially available. The conjugates are hydrolytically stable and the PEGylation reactions can be performed at neutral pH.

As discussed above, cysteine residues in most proteins participate in disulfide bonds (essential disulfides) and are not available for derivatization. However, any free cysteine in a protein or peptide, including a free cysteine that occurs in the native (wild-type) protein, a free cysteine that is created by deleting or substituting a non-cysteine residue for one cysteine in a non-essential disulfide, or a newly added "free" cysteine (e.g., as a result of substitution of a cysteine for a non-cysteine residue or the insertion of a cysteine into a protein or peptide), will serve as the site for the specific attachment of a PEG molecule, thus avoiding the product heterogeneity that is often seen with amine PEGylation reactions. The added cysteine must be exposed on the protein's surface and be accessible for PEGylation for this method to be successful. If the chosen site is non-essential (e.g. for proper folding or biological activity of the protein), then the PEGylated protein will display wild type (normal) or near wild type in vitro bioactivity.

A free thiol group can also be introduced into the primary amino acid sequence of a protein by chemical modification of lysine. One such example involves treatment of the protein with Traut's reagent (2-Iminothiolane hydrochloride). Alternatively the protein can be treated with reagents such as N-succinimidyl S-acetylthioacetate (SATA) or N-succinimidyl S-acetylthiopropionate (SATP) that introduce a protected sulfhydryl which can be deprotected prior to exposure to a thiol reactive PEG. Alternatively, a "free" cysteine can be introduced by deleting or mutating a native cysteine (that normally forms a disulfide bond) to another amino acid such as a serine or alanine so that an odd number of cysteines are present in the protein's primary sequence.

It is also possible to genetically introduce two or more additional cysteines that are not able to disulfide bond with each other. In this case, two PEGs can be specifically attached to the protein. Alternatively, a native disulfide bond can be reduced, resulting in two free cysteine residues that are available for thiol specific PEGylation. Free thiol groups can also be introduced by chemical conjugation of a peptide to a protein where the peptide contains a free cysteine group or a cysteine group modified with a reversible thiol-blocking agent.

Carboxyl-reactive PEGs for PEGylation

PEG-hydrazide can be used to PEGylate the carboxyl groups of amino acids in presence of N,N'-dicyclohexylcarbodiimide (DCC), or in presence of a water soluble coupling agent such as N-(-3 dimethylaminopropyl)-N'-ethylcarbodiimide hydrochloride (EDC). The carboxyl groups of a protein when activated with EDC at an acidic pH (pH 4.5-5) react readily with PEG-hydrazide, whereas amino groups of the protein are protonated and unreactive. Dimeric IFN-γ has 20 aspartic acids (D2, D21, D24, D41, D61, D62, D76, D90, D91 and D102) and 18 glutamic acids (E7, E9, E38, E39, E71, E75, E93, E112 and E119).

PEGylation of Unnatural Amino Acids

Similar to the genetically engineered cysteine mutations for site-specific PEGylation, researchers have reported the specific incorporation of unnatural amino acids into proteins expressed in yeast, in E. Coli and in mammalian cells (Deiters et al., 2004). Specifically para-azidophenylalanine was substituted into a protein at certain sites determined by the positioning of the amber codon. The reactive group on the amino acid analog was used in a mild [3+2] cycloaddition reaction with an alkyne derivatized PEG reagent to allow for site-specific conjugation.

Arginine-reactive PEGs for PEGylation

Another approach is the attachment of the PEG moiety on the arginine side chain using PEG-1-3-dioxo compounds such as PEG-phenylglioxate. The disadvantages of this approach include long reaction times and limited specificity since other amino acids such as histidine and lysine, may be modified as well. Dimeric IFN-γ has 16 arginines (R42, R89, R107, R129, R131, R137, R139, and R140).

Hydroxyl-reactive PEGs for PEGylation

PEG-isocyanate can be used to attach a PEG to a hydroxy group via a stable urethane linkage. The disadvantage of this approach is lack of specificity since it is also capable of reacting with amines. Thus, this reagent is more commonly used in PEGylation reactions involving polysaccharides or non-peptide drugs.

Oxidized Carbohydrate-reactive PEGs for PEGylation

Oxidation of the carbohydrate residues or N-terminal serine or threonine is an alternative method for a site-specific PEGylation. Carbohydrate side chains can be oxidized with enzymes or chemically with sodium periodate to generate reactive aldehyde groups. These sites can be reacted with either PEG-hydrizide or PEG-amine to produce a reversible Schiff's base. These linkages are then reduced with sodium cyanoborohydride to a more stable alkyl hydrazide or in the case of the Schiff's base, a secondary amine. Multiple attachment sites are generated by this method but the PEG is localized on the carbohydrate chain rather than on the protein.

A similar approach takes advantage of an N-terminal serine or threonine. These amino acid residues can be converted by periodate oxidation to a glyoxylyl derivative that will also react with PEG-hydrazide or PEG-amine. IFN-γ variants in which a serine or threonine residue is added preceding Q1 or substituted for Q1 are contemplated by this invention.

Enzymatically Catalyzed PEGylation Reagents

Another approach for PEGylation of proteins uses trans-glutaminase to modify glutamine residues so that they become reactive with alkylamine derivatives of PEG (Sato 2002). Dimeric IFN-γ has 18 glutamines (Q1, Q45, Q47, Q64, Q67, Q106, Q115, Q133, and Q143).

N-Terminal PEGylation for Proteins Containing an N-Terminal Cysteine or N-Terminal Histidine IFN-γ can be modified to contain an N-terminal cysteine or N-terminal histidine which can be specifically PEGylated on the N-terminal amine using an o-pyridylthioester PEG reagent (Nektar). The reagent initially reacts with the amino acid side chain followed by a chemical rearrangement that results in an amide linkage between the PEG and the amino group of the N-terminal amino acid.

Multifunctional PEGs

While a majority of the PEGylated proteins currently on the market have one or more PEGs per protein, it is also possible to construct protein conjugates with two or more proteins attached to one PEG moiety. Difunctional and heterofunctional PEGs are commercially available and can be used to covalently link two or more IFN-γ variants.

Bioactive Peptides of the Invention, and Polymer Conjugates Thereof

One embodiment of the present invention relates to PEGylated bioactive peptides, and particularly, PEGylated cysteine variants of bioactive peptides, and to any homologues thereof, or truncated forms thereof. In one aspect, the bioactive peptide is a peptide wherein the native protein contains no essential disulfides, and wherein the peptide contains, or has been modified to contain, at least one free cysteine. In one embodiment, such a bioactive peptide is produced by a method of the invention. In another aspect, the invention relates to bioactive peptides that are PEGylated variants of a peptide selected from the group consisting of glucagon, glucagon-like peptide-1 (GLP-1), GLP-2, Gastric inhibitory peptide (GIP), PYY, exendin, ghrelin, gastrin, amylin, and oxyntomoldulin.

Another embodiment of the present invention relates to a composition comprising any one or more of the above-described polymer conjugated or non-conjugated variants of the bioactive peptides, including cysteine variants, homologues thereof, or truncated forms thereof, and a pharmaceutically acceptable carrier.

Yet another embodiment of the present invention relates to a cysteine variant of any of glucagon, glucagon-like peptide-1 (GLP-1), GLP-2, Gastric inhibitory peptide (GIP), PYY, exendin, ghrelin, gastrin, amylin, and oxyntomoldulin, such as those described in detail in the Examples, or a homologue or truncated form thereof, wherein a cysteine residue is substituted for at least one amino acid in the peptide. Preferred sites for cysteine substitution are described in Examples 11-19.

In one aspect of this embodiment, the substituted or inserted cysteine residue is modified with a cysteine-reactive moiety. In another aspect, the substituted or inserted cysteine residue is modified with polyethylene glycol.

Another embodiment of the present invention relates to a composition comprising any one or more (at least 2, 3, 4, 5, 6, 7, 8, 9 or 10) of the above-described variants and a pharmaceutically acceptable carrier.

Many bioactive peptides have been described, including glucagon, glucagon-like peptide-1 (GLP-1), GLP-2, Gastric inhibitory peptide (GIP), PYY, exendin, ghrelin, gastrin, amylin, and oxyntomoldulin. These peptides typically are 10-40 amino acids in length and most do not contain cysteine residues. Methods to develop longer acting forms of these peptides are desired. In the following Examples we provide novel analogs of these peptides that may be used to create longer acting versions of the peptides. The longer-acting peptides are useful because they can be administered lat lower doses and less frequently than the unmodified peptides. Preferred analogs are ones in which a cysteine residue has been introduced into the peptide sequence either by substitution for a native amino acid or by insertion preceding the first amino acid or following the last amino acid of the peptide. Cysteine residues also can be inserted between two adjacent amino acids in the peptide chain. The added cysteine residue can be modified with a cysteine reactive moiety such as a cysteine-reactive polymer. Useful cysteine reactive polymers include, but are not limited to cysteine-reactive polyethylene glycols (PEGs), dextrans, sugars, and starches. PEGs can be linear or branched PEGs. Other useful cysteine-reactive moieties for modifying the peptides include but are not limited to cysteine-reactive lipids, labels, dyes, lipids, chromphores, and radionucleotides. Preferred reactive groups on the cysteine-reactive moieties include maleimide, vinylsulfone and iodoacetamide groups. The methods described herein are particularly useful for modifying peptides that do not contain a native cysteine residue (s) with a cysteine-reactive moiety such as a cysteine-reactive PEG. These methods also can be used to modify peptides that do contain one or more native cysteine residues. These methods also are useful for creating longer-acting antagonist analogs of peptides.

Alternatively, the peptides can be modified with amine-reactive moieties such as amine-reactive polymers, labels, dyes, lipids, chromphores, and radionucleotides. Useful amine-reactive polymers include, but are not limited to, amine-reactive PEGs, dextrans, sugars and starches. Typically amine-reactive moieties attach to lysine residues or the N-terminal amino acid. Labeling of the peptides can be made more specific for lysine residues or the N-terminus by substituting non-lysine amino acids, preferably arginine, for one or more lysine residues in the protein. Additionally, new lysine residues can be engineered into the peptides to create new sites for modification of the peptides. New lysine residues can be added to the protein by substitution for a non-lysine residue or by insertion preceding the first amino acid of the peptide or following the last amino acid of the peptide. Lysine residues also can be inserted between two adjacent amino acids in the peptide chain. These methods also are useful for creating longer-acting agonist and antagonist analogs of peptides.

Methods for modifying a protein with a variety of polymers, including at cysteine and lysine residues, have been described above and are encompassed by this embodiment of the invention.

As used herein the term analog comprises a variety of modifications that can be made to a protein. Such changes may include amino acid variants, deletions, additions, insertions, fusion proteins, and covalent and non-covalent modifications.

Also encompassed by the invention is to the use of any variant of a bioactive peptide described herein, including any polymer-variant conjugate (e.g., a PEGylated bioactive peptide, including a monoPEGylated bioactive peptide) in a therapeutic method or in the preparation of a medicament, such as for the treatment of a disease or condition in which the use of the native bioactive peptide would be useful. Such diseases and conditions are described for multiple bioactive peptide variants of the invention in the Examples.

IFN-γ Conjugates of the Invention

One embodiment of the present invention relates to PEGylated IFN-γ variants, and particularly, a PEGylated IFN-γ cysteine variant, and to any homologues thereof, or truncated forms thereof. In one aspect of this embodiment, the IFN-γ variant is a variant of a native IFN-γ protein comprising an amino acid sequence of SEQ ID NO:1 or SEQ ID NO:2, with SEQ ID NO:1 being preferred.

Another embodiment of the present invention relates to a composition comprising any one or more of the above-described PEGylated IFN-γ variants, homologues thereof, or truncated forms thereof, and a pharmaceutically acceptable carrier.

Yet another embodiment of the present invention relates to a cysteine variant of IFN-γ (SEQ ID NO:1) or a homologue or truncated form thereof, wherein a cysteine residue is substituted for at least one amino acid located in at least one region of IFN-γ.

In one aspect of this embodiment, the substituted or inserted cysteine residue is modified with a cysteine-reactive moiety. In another aspect, the substituted or inserted cysteine residue is modified with polyethylene glycol.

Another embodiment of the present invention relates to a composition comprising any one or more (at least 2, 3, 4, 5, 6, 7, 8, 9 or 10) of the above-described variants and a pharmaceutically acceptable carrier.

Native IFN-γ is a homodimeric N-glycosylated protein with 143 amino acids, no cysteine residues (i.e., no natural disulfides) and an isoelectric point of about 8.7. The amino acid sequence of the mature human IFN-γ protein is represented herein by SEQ ID NO:1, and the amino acid sequence of the mature murine IFN-γ protein is represented herein by SEQ ID NO:2. Amino acid variants and truncated forms of IFN-γ have been described (Van Dan Haze et al., 2005). When expressed in *E. coli*, the protein may contain an N-terminal methionine not found in the native protein.

IFN-γ is enriched in basic amino acids with 40 lysines and 16 arginines per dimer. There are two potential glycosylation sites at N25 and N97. The absence of carbohydrate moieties in *E. coli*-derived recombinant IFN-γ does not affect its biological activity but it does have an effect on both its physicochemical and pharmacokinetic properties (Arakawa et al., 1985). Unlike the other IFN family members, IFN-γ is extremely acid sensitive. Between pH 3.5 and 4.5, the protein loses structural integrity and rapidly aggregates. At pH 2.3, an acid-labile bond is broken with subsequent loss of all anti-viral activity (Mulkerrin and Wetzel, 1989). IFN-γ is also heat sensitive and undergoes irreversible thermal denaturation and aggregation in solution at temperatures greater than 40° C. (Beldarrain et al., 1999).

The X-ray crystal structure of recombinant human IFN-γ has been determined for both the protein itself (Ealick et al., 1991, *Science* 252: 698-702) and in complex with the IFN-γ receptor alpha subunit (IFN-γRα) (Walter et al., 1995). IFN-γ is primarily alpha helical (~62%) with no beta sheets. IFN-γ contains six alpha helical regions (helices A-F) that are joined by short unstructured sequences or loops. Ealick et al., supra, identifies the helical and non-helical regions of human gamma interferon (FIG. 3 of Ealick et al.), wherein the positions of the helical regions and the intervening (loop) regions, as well as the region preceding Helix A and following Helix E, are located at the following positions in the human gamma interferon amino acid sequence (SEQ ID NO:1): amino acids 4-15 (helix A), amino acids 28-36 (helix B), amino acids 41-62 (helix C), amino acids 68-82 (helix D), amino acids 87-98 (helix E) and amino acids 104-121 (helix F). The region preceding helix A accordingly encompasses amino acids 1-3, the A-B loop encompasses amino acids 16-27, the B-C loop encompasses amino acids 37-40, the C-D loop encompasses amino acids 63-67, the D-E loop encompasses amino acids 83-86, the E-F loop encompasses amino acids 99-103, and the region following helix F encompasses amino acids 122-143.

IFN-γ exists as a dimer in solution that is stabilized by the intertwining of the helices across the subunit interface with multiple intersubunit interactions. The first four helices (A-D) from one subunit form a cleft that accommodates helix F of the other subunit. There are numerous hydrophobic contacts among all of the helices, but most are between the C and D helices. The C helix is the most hydrophobic helix and is essentially buried in the core of the dimer. Overall, the IFN-γ dimer has a "V"-like conformation with the amino and carboxyl regions of each monomer being juxtaposed to one another.

Preferred Sites for Thiol-specific PEGylation of IFN-γ

In general, a cysteine substitution can be made for any amino acid that is 1) located on the surface of IFN-γ, 2) not required for the structural integrity of IFN-γ and 3) not required for receptor binding. Non-essential amino acids can be identified by performing cysteine-scanning mutagenesis on the target protein and measuring effects on biological activity. Cysteine-scanning mutagenesis entails adding or substituting cysteine residues for individual amino acids in the polypeptide chain and determining the effect of the cysteine substitution on biological activity. Cysteine scanning mutagenesis is similar to alanine-scanning mutagenesis (Cunningham et al., 1991), except that target amino acids are individually replaced with cysteine rather than alanine residues.

Glycosylation sites and glycosylation recognition sequences are attractive sites for attaching PEG molecules because these sites are surface exposed and the natural protein can tolerate bulky sugar groups at these positions. The human IFN-γ sequence contains two potential N-linked glycosylation sites at asparagine 25 and asparagine 97. Asparagine 25 is located at the C-terminal end of the A-B loop. Aspargine 97 is located at the C-terminal end of Helix E. Tang et al. (1996) described the PEGylation of an IFN-γ variant in which asparagine 97 was mutated to a cysteine residue. The N- and C-termini regions of IFN-γ are also possible sites for site-directed PEGylation, including adding a cysteine that precedes the first amino acid or follows the last amino acid of IFN-γ. Cysteine insertions between two adjacent amino acids within the primary amino acid sequence of IFN-γ are also reasonable sites for thiol specific PEGylation if the biological activity or protein's conformation is not significantly affected by the cysteine insertions. Preferred sites for cysteine substitutions include the region preceding helix A (Q1, D2, P3), the A-B loop region (N16, A17, G18, H19, S20, D21, V22, A23, D24, N25, G26), the B-C loop region (K37, E38, E39, S40), the C-D loop region (D63, Q64, S65, I66, Q67), the D-E loop region (N83, S84, N85, K86), the E-F loop region (N97, Y98, S99, V100, T101, D102, L103) and the region following Helix F (P122, A123, A124, K125, T126, G127, K128, R129, K130, R131, S132, Q133, M134, L135, F136, R137, G138, R139, R140, A141, S143, Q143). Cysteine residues also can be added preceding the protein's first amino acid or following the last amino acid. These IFN-γ cysteine variants can be incorporated into the native IFN-γ sequence or in variants in which Q1, D2, or Q1 and D2 are deleted or changed to non-glutamic or non-aspartic acids, respectively. Possible substitutions include amino acids such as alanine, arginine, aspartic acid (for Q1 only), asparagine, glutamic acid, glutamine (for D2 only), glycine, histidine, isoleucine, leucine, lysine, methionine, phenylalanine, proline, serine, threonine, tryptophan, tyrosine, or valine).

Therapeutic Uses for Long Acting IFN-γ Proteins

Another embodiment of the invention relates to the use of any IFN-γ variant described herein, including any polymer IFN-γ variant conjugate (e.g., a PEGylated, including a monoPEGylated IFN-γ) in a therapeutic method or in the preparation of a medicament, such as for the treatment of a disease or condition in which the use of native IFN-γ would be useful. A long acting form of IFN-γ would be useful for the treatment of a number of immunological, viral, and neoplastic diseases, including diseases currently treated with IFN-γ. Recombinant IFN-γ is currently approved by the FDA for reducing the frequency and severity of serious infections associated with chronic granulomatous disease (CGD) and for delaying time to disease progression in patients with severe malignant osteopetrosis. CGD is a group of rare, inherited disorders of the immune system that are caused by defects in the phagocytes. These defects leave patients vulnerable to severe reoccurring bacterial and fungal infections along with chronic inflammatory conditions.

Malignant osteopetrosis is an inherited disorder, characterized by an osteoclast defect leading to bone overgrowth and deficient phagocyte oxidative metabolism. This life-threatening disorder leads to blindness, deafness by six months of age and an increase in susceptibility to infection. Treatment with IFN-γ has proven to be effective in delaying disease progression from a median time of 65 days after birth for the control group to 165 days for the treatment group (Key et al., 1995).

A long acting form of IFN-γ is useful for treating Idiopathic Pulmonary Fibrosis (IPF), which is a disorder that is characterized by progressive scarring or fibrosis of the lungs, which ultimately leads to death. Another potential indication for a long acting form of IFN-γ is cancer and in particular, ovarian cancer where current treatment with chemotherapy alone has a five-year survival rate of only 44%. In in vitro and in vivo studies, IFN-γ has been shown to be directly toxic to cancer cells, including ovarian cancer cells, neuroblastoma cancer cells, and Ewings Sarcoma cancer cells, and to stimulate the body's immune system to enhance the removal of cancer cells (see review by Wall et al., 2003). In vitro and in vivo studies have shown that IFN gamma may be useful as an anti-cancer agent alone and in combination with proteins that cause cell death such as TRAIL and TRAIL receptor ligand agonists (Yang et al., 2003; Merchant et al., 2004). IFN gamma induces expression of cell death proteases such as caspase-8 in many tumor cells and may be useful in combination with other anti-cancer compounds that require or use the caspase-8 cell death pathway to kill tumor cells. IFN gamma also may be useful as an anti-cancer agent in combination with chemotherapeutic agents that induce TRAIL receptor [either Trail Receptor 1 (TR1) or Trail Receptor 2 (TR2) or both) expression on tumor cells. IFN gamma can inhibit proliferation and survival of cancer cells directly, or by inhibiting their metastasis to other tissues and organs. A long acting form of IFN-γ may be useful for treating liver fibrosis, asthma, and lymphomas, and IFN-γ also may prove to be an effective treatment against biological warfare agents. Preclinical data has confirmed IFN-γ's ability to protect against both small pox and tularaemia in animal models (Liu, 2003; Anthony et al., 1989). A long acting form of IFN-γ may be useful in the treatment of small pox, anthrax, plague, botulism, tularaemia, and hemorrhagic fevers.

A long acting form of IFN-γ can also be used alone or synergistically in combination with other anti-fungal, anti-viral, anti-bacterial or anti-tumor agents. For example, IFN-α and IFN-γ, while functionally related, bind to different cell surface receptors (See review by Lau et al., 2002). In in vitro cells-based assays and in vivo animal studies, combinations of IFN-α and -γ show enhanced anti-viral and anti-tumor activities than either drug alone (Larkin et al. 2003; Fleischmann et al., 1998; Yanai et al., 2001). Antifungal agents have been evaluated in conjunction with IFN-γ and shown to be effective in previously unresponsive patients (Summers et al., 2005).

A long acting form of IFN-γ or composition comprising the same of the present invention is administered to an animal in a manner effective to deliver the composition to a target cell, a target tissue, or systemically to the animal, whereby provision of a therapeutic benefit is achieved as a result of the administration of the IFN-γ or composition. Suitable administration protocols include any in vivo or ex vivo administration protocol. According to the present invention, suitable methods of administering a composition of the present invention to a patient include any route of in vivo administration that is suitable for delivering the composition into a patient. The preferred routes of administration will be apparent to those of skill in the art, depending on the type of condition to be prevented or treated and/or the target cell population.

Compositions and Therapeutic Methods of the Invention

Any of the proteins or peptides described herein or produced by the methods of the invention, including long acting (e.g., PEGylated) forms of the proteins or peptides, can be used in various compositions and therapeutic methods. Generally, the proteins and peptides of the invention can be used in any method, including any therapeutic method, that is useful with the native (unmodified, wild-type) protein or peptide.

Cysteine muteins and PEGylated proteins and peptides of the present invention are preferably administered in a composition. Compositions can include a cysteine mutein (cysteine variant) of the invention and any other suitable pharmaceutically acceptable carrier, as well as, in some aspects, additional components that may be useful in the treatment of a give disease or condition. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably any site where the cysteine mutein will provide a detectable effect as compared to in the absence of the mutein, and includes a disease site or a site of cell types to be contacted with the mutein. Preferred pharmaceutically acceptable carriers are capable of maintaining the mutein of the present invention in a form that, upon arrival of the mutein at the cell target in a culture or in patient, the mutein is capable of interacting with its target (e.g., platelets or progenitor cells thereof).

Suitable excipients of the present invention include excipients or formularies that transport or help transport, but do not specifically target a composition to a cell or area (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a cysteine mutein of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphere, and transdermal delivery systems. Other carriers of the present invention include liquids that, upon administration to a patient, form a solid or a gel in situ. Preferred carriers are also biodegradable (i.e., bioerodible). In the event that a cysteine mutein of the invention is administered as a recombinant nucleic acid molecule encoding the cysteine mutein (e.g., gene therapy or genetic immunization), suitable carriers include, but are not limited to liposomes, viral vectors or other carriers, including ribozymes, gold particles, poly-L- lysine/DNA-molecular conjugates, and artificial chromosomes. Natural lipid-containing carriers include cells and cellular membranes. Artificial lipid-containing carriers include liposomes and micelles.

A carrier of the present invention can be modified to target to a particular site in a patient, thereby targeting and making use of a compound of the present invention at that site. A pharmaceutically acceptable carrier which is capable of targeting can also be referred to herein as a "delivery vehicle" or "targeting carrier". Suitable modifications include manipulating the chemical formula of the lipid portion of the delivery vehicle and/or introducing into the vehicle a targeting agent capable of specifically targeting a delivery vehicle to a preferred site or target site, for example, a preferred cell type. A "target site" refers to a site in a patient to which one desires to deliver a composition. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One delivery vehicle of the present invention is a liposome. A liposome is capable of remaining stable in an animal for a sufficient amount of time to deliver a nucleic acid molecule or protein described in the present invention to a preferred site in the animal. A liposome, according to the present invention, comprises a lipid composition that is capable of delivering a nucleic acid molecule or protein to a particular, or selected, site in a patient. A liposome according to the present invention comprises a lipid composition that is capable of fusing with the plasma membrane of the targeted cell to deliver a nucleic acid molecule or protein into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or protein of the present invention can be achieved using methods standard in the art.

Another type of delivery vehicle, when the cysteine mutein is administered as a nucleic acid encoding the mutein, comprises a viral vector. A viral vector includes an isolated nucleic acid molecule, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

According to the present invention, an effective administration protocol (i.e., administering a therapeutic composition in an effective manner) comprises suitable dose parameters and modes of administration that result in the desired effect in the patient (e.g., stimulation of platelet production), preferably so that the patient is protected from the disease (e.g., by disease prevention or by alleviating one or more symptoms of ongoing disease). Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that results in the desired therapeutic effect in the patient, depending on the cysteine mutein that is administered, or in the amelioration of at least one symptom of a condition in the patient, when administered one or more times over a suitable time period. Doses can vary depending upon the disease being treated. One of skill in the art can readily determine appropriate single dose sizes for a given patient based on the size of a patient and the route of administration.

In one aspect of the invention, a suitable single dose of a therapeutic composition of the present invention is an amount that, when administered by any route of administration, provides a therapeutic effect in the patient as described above, as compared to a patient which has not been administered with the therapeutic composition of the present invention (i.e., a control patient), as compared to the patient prior to administration of the composition, or as compared to a standard established for the particular disease, patient type and composition.

In one aspect of the invention an appropriate single dose of a cysteine mutein of the present invention is at least about 0.01 micrograms per kg of the animal to which the mutein is administered, and in other aspects, at least about 0.1 micrograms/kg, at least about 0.2 micrograms/kg, at least about 0.5 micrograms/kg, at least about 1 micrograms/kg, at least about 5 micrograms/kg, at least about 10 micrograms/kg, at least about 25 micrograms/kg, at least about 50 micrograms/kg, at least about 75 micrograms/kg, at least about 100 micrograms/kg, at least about 200 micrograms/kg, at least about 300 micrograms/kg, at least about 400 micrograms/kg, at least about 500 micrograms/kg, at least about 750 micrograms/kg, at least about 1 mg/kg, or at least about 5 mg/kg.

As discussed above, a therapeutic composition of the present invention is administered to a patient in a manner effective to deliver the composition to a cell, a tissue, and/or systemically to the patient, whereby the desired result is achieved as a result of the administration of the composition. Suitable administration protocols include any in vivo or ex vivo administration protocol. The preferred routes of administration will be apparent to those of skill in the art, depending on the type of condition to be prevented or treated; whether the composition is nucleic acid based or protein based; and/or the target cell/tissue. For proteins or nucleic acid molecules, preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue. Routes useful for deliver to mucosal tissues include, bronchial, intradermal, intramuscular, intranasal, other inhalatory, rectal, subcutaneous, topical, transdermal, vaginal and urethral routes. Combinations of routes of delivery can be used and in some instances, may enhance the therapeutic effects of the composition. Particularly preferred routes of delivery include subcutaneous and intravenous delivery.

Ex vivo administration refers to performing part of the regulatory step outside of the patient, such as administering a composition of the present invention to a population of cells removed from a patient under conditions such that the composition contacts and/or enters the cell, and returning the cells to the patient. Ex vivo methods are particularly suitable when the target cell type can easily be removed from and returned to the patient.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers include plastic capsules or tablets such as those known in the art.

One method of local administration is by direct injection. Direct injection techniques are particularly useful for administering a composition to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention.

In the method of the present invention, compositions can be administered to any animal and preferably, to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, sheep, cattle, horses and pigs, with humans being particularly preferred.

General Definitions

As used herein, reference to an isolated protein or polypeptide in the present invention, including an IFN-γ protein described particularly herein, includes full-length proteins, fusion proteins, or any fragment (truncated form) or homologue of such a protein. Such a protein can include, but is not limited to, purified proteins, recombinantly produced proteins, membrane bound proteins, proteins complexed with lipids, soluble proteins and isolated proteins associated with other proteins. More specifically, an isolated protein according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. In addition, and again by way of example, a "human IFN-γ protein" or a protein "derived from" a human IFN-γ protein refers to a IFN-γ protein (generally including a homologue of a naturally occurring IFN-γ protein) from a human (*Homo sapiens*) or to a IFN-γ protein that has been otherwise produced from the knowledge of the structure (e.g., sequence) and perhaps the function of a naturally occurring IFN-γ protein from *Homo sapiens*. In other words, a human IFN-γ protein includes any IFN-γ protein that has substantially similar structure and function of a naturally occurring IFN-γ protein from *Homo sapiens* or that is a biologically active (i.e., has biological activity) homologue of a naturally occurring IFN-γ protein from *Homo sapiens* as described in detail herein. As such, a human IFN-γ protein can include purified, partially purified, recombinant, mutated/modified and synthetic proteins. According to the present invention, the terms "modification" and "mutation" can be used interchangeably, particularly with regard to the modifications/mutations to the amino acid sequence of protein (or nucleic acid sequences) described herein. An isolated protein useful as an antagonist or agonist according to the present invention can be isolated from its natural source, produced recombinantly or produced synthetically.

As used herein, the term "homologue" is used to refer to a protein or peptide which differs from a naturally occurring protein or peptide (i.e., the "prototype" or "wild-type" protein) by modifications, including minor modifications, to the naturally occurring protein or peptide, but which maintains the basic protein and side chain structure of the naturally occurring form. Such changes include, but are not limited to: changes in one or a few (i.e., 1, 2, 3, 4, 5, 6, 7, 8, 9 or 10) amino acid side chains; changes one or a few amino acids, including deletions (e.g., a truncated form of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. A cysteine variant of IFN-γ is a homologue of IFN-γ, by way of example.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

In one embodiment, a homologue of a given protein comprises, consists essentially of, or consists of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

According to the present invention, an isolated IFN-γ protein, including a biologically active homologue or fragment thereof, has at least one characteristic of biological activity of activity the wild-type, or naturally occurring IFN-γ protein (which can vary depending on whether the homologue or fragment is an agonist or antagonist of the protein, or whether an agonist or antagonist mimetic of the protein is described). In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications, activities or interactions which result in a decrease in protein expression or a decrease in the activity of the protein, can be referred to as inactivation (complete or partial), down-regulation, reduced action, or decreased action or activity of a protein. Similarly, modifications, activities or interactions which result in an increase in protein expression or an increase in the activity of the protein, can be referred to as amplification, overproduction, activation, enhancement, up-regulation or increased action of a protein. The biological activity of an IFN-γ protein according to the invention can be measured or evaluated using any assay for the biological activity of the protein as known in the art. Such assays are known in the art, and assays for IFN-γ activity are described in the Examples.

In accordance with the present invention, an isolated polynucleotide (also referred to as an isolated nucleic acid molecule) is a nucleic acid molecule that has been removed from its natural milieu (e.g., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. A polynucleotide useful in the present invention can include a portion of a nucleic acid sequence (sense or non-sense strand) that is suitable for use as a hybridization probe or PCR primer for the identification of a full-length gene (or portion thereof), or to encode a protein or fragment (truncated form) or homologue thereof. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

The minimum size of a nucleic acid molecule or polynucleotide of the present invention is a size sufficient to encode a protein having a desired biological activity, or sufficient to form a probe or oligonucleotide primer that is capable of forming a stable hybrid with the complementary sequence of a nucleic acid molecule encoding the natural protein (e.g., under moderate, high or very high stringency conditions). If the polynucleotide is an oligonucleotide probe or primer, the size of the polynucleotide can be dependent on nucleic acid composition and percent homology or identity between the nucleic acid molecule and a complementary sequence as well as upon hybridization conditions per se (e.g., temperature, salt concentration, and formamide concentration). The minimum size of a polynucleotide that is used as an oligonucleotide probe or primer is at least about 5 nucleotides in length, and preferably ranges from about 5 to about 50 or about 500 nucleotides or greater, including any length in between, in whole number increments (i.e., 5, 6, 7, 8, 9, 10, . . . 33, 34, . . . 256, 257, . . . 500). There is no limit, other than a practical limit, on the maximal size of a nucleic acid molecule of the present invention, in that the nucleic acid molecule can include a portion of a protein-encoding sequence or a nucleic acid sequence encoding a full-length protein.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

In one embodiment of the present invention, any of the amino acid sequences described herein, including homologues of such sequences (e.g., cysteine muteins), can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

The following examples are provided for the purpose of illustration and are not intended to limit the scope of the present invention.

EXAMPLES

Example 1. Cloning and Expression of Human IFN-γ and Cysteine Muteins of IFN-γ

A cDNA encoding human IFN-γ was amplified by RT-PCR from total RNA isolated from the human Jurkat T cell line (American Type Culture Collection, Rockville, Md.). The cells were grown in RPMI media supplemented with 10% FBS, 50 units/ml penicillin and 50 µg/ml streptomycin. The cells were activated in vitro for 6 hours with 1 µg/ml PHA-L and 50 ng/ml PMA (phorbol 12-myristate 13-acetate), to induce IFN-γ expression prior to RNA isolation (Weiss et al., 1984; Wiskocil et al., 1985). RNA was isolated from the cells using an RNeasy Mini RNA isolation kit purchased from Qiagen, Inc. First strand synthesis of single-stranded cDNA was accomplished using a 1st Strand cDNA Synthesis Kit for RT-PCR (AMV) from Boehringer Mannheim Corp. (Indianapolis, Ind.) and random hexamers were used as the primer. Subsequent PCR reactions using the products of the first strand synthesis as template were carried out with forward primer BB112 (5'-CGCAA GCTTG CCACC ATGAA ATATA CAAGT TATAT C-3'; SEQ ID NO:3) and reverse primer BB113 (5'-CGCGG ATCCT CCGGA CTGGG ATGCT CTTCG ACCTT G-3'; SEQ ID NO:4). Primer BB112 anneals to the 5' end of the coding sequence for the IFN-γ secretion signal and the reverse primer, BB113, anneals to the 3' end of the IFN-γ coding sequence. The resulting PCR product was digested with Hind III and Bam HI, gel purified and cloned into pcDNA3.1 (+) vector that had been digested with Hind III and Bam HI, alkaline phosphatase treated, and gel purified. A clone with the correct DNA sequence (Gray et al., 1982) was designated pBBT192.

The gene for IFN-γ in pBBT192 was next modified by PCR for expression in *E. coli*. Primers were synthesized that anneal to the 5' and 3' ends of the gene, and incorporate sequences for translational initiation and termination. The modification of the gene was performed in two steps. Forward primer BB1049 (5'CAG GAC CCA TAC GTA AAA GAA GCA GAA AAC CTT AAG; SEQ ID NO:5), and reverse primer BB1050 (5'CCG GAATTC TTA CTG GGA TGC ACG TCG ACC TTG AAA CAG; SEQ ID NO:6) were used to incorporate a TAA termination codon and EcoRI recognition site (GAATTC) at the 3' end of the gene. The product of this PCR was then amplified using forward primer BB1048 (5' CGC GGA TCC ATC TTG GAG GAT GAT TAA ATG CAG GAC CCA TAC GTA AAA G; SEQ ID NO:7) and reverse primer BB1050 to incorporate an ATG initiation codon and a BamHI recognition site (GGATCC) for cloning into pET21a+, a T7 promoter expression vector (Novagen). The product of this second PCR was gel purified, digested with BamHI and EcoRI, repurified, and cloned into pUC19 that had been digested with BamHI and EcoRI, alkaline phosphatase (AP) treated, and purified using a Qiagen PCR purification kit. A plasmid with the expected sequence was named pBBT939. For expression experiments, this plasmid was introduced into *E. coli* strain BL21 (DE3) (Invitrogen).

Mutagenesis of IFN-γ was performed by PCR using methods described by Scharf (1999) or by Higuchi (1999). For targeted residues whose codons were close to the unique BsaI restriction site in pBBT939 at residues E71 and T72, the inventors employed the method of Scharf, in which one mutagenic oligonucleotide and one PCR reaction was required. For other targeted residues, Higuchi's method, using two mutagenic oligonucleotides, was employed. Higuchi's method requires three PCRs; two reactions that produce a "left" fragment and a "right" fragment, and a final "splicing" reaction, in which the left and right fragments are mixed and amplified with the two outside primers containing the restriction sites.

Similar methods were used to construct IFN gamma muteins N25C, K37C, Q67C and N83C, as well as an IFN gamma mutein, in which Q1 is deleted. Similar methods can be used to construct IFN gamma cysteine muteins Q1C, D2C, and P3C. Similar methods also can be used to construct cysteine muteins in which a cysteine residue is inserted preceding the first amino acid of the mature protein, Q1, or following the last amino acid of the protein, Q143. Cysteine analogs of IFN gamma are contemplated in the context of the wild type gamma interferon sequence or in the context of the sequences of other gamma interferon analogs, such as those containing other amino acid substitutions, deletions or additions. One preferred set of gamma interferon analogs are those in which Q1, D2, P3, or a combination of these amino acids, are deleted.

PCR products were digested with either Eco RI and Bam HI, BamHI and BsaI, or EcoRI and BsaI, and cloned into similarly digested and AP-treated pBBT939. The newly cloned fragment was sequenced to confirm that the desired cysteine substitution mutation was in place and that no unexpected mutations were present.

BamHI/EcoRI fragments encoding wild-type IFN-γ or IFN-γ cysteine muteins were isolated after sequencing and ligated into BamHI/EcoRI/AP-digested and purified pET21a+ (Novagen). The ligation reaction was transformed into the *E. coli* strain JM109 (Promega). Plasmids from ampicillin-resistant colonies were analyzed for the correct size of insert, and transformed into BL21 (DE3) (Invitrogen). Expression of native IFN-γ and IFN-γ cysteine muteins results in the presence of an N-terminal methionine upstream of glutamine-1 (Q1) in the sequence.

Example 2. Eukaryotic Expression of Recombinant IFN-γ and the IFN-γ Cysteine Variants IFN-γ and the IFN-γ cysteine muteins can also be expressed as intracellular or secreted proteins in eukaryotic cells such as yeast, insect cells or mammalian cells. Vectors for expressing the proteins and methods for performing such experiments are described in catalogues from various commercial supply companies such as Invitrogen, Inc., Stratagene, Inc. and CloneTech, Inc. Procedures for expression proteins in insect and mammalian cells are described in Cox et al., 2001.

Example 3. Small Scale Preparation of Wild Type IFN-γ and the IFN-γ Cysteine Variants in *E. coli*

The strains containing wild type IFN-γ or IFN-γ variants were grown overnight in Luria Broth (LB media) containing 100 µg/ml ampicillin and 1% glucose at 37° C. in roll tubes. Saturated overnight cultures were diluted to an OD at 600 nm of ~0.025 in the same media and incubated at 37° C. in shake flasks. Typically a 400 ml culture was grown in a 2 L shake flask. When culture ODs reached ~0.5-0.6, IPTG was added to a final concentration of 0.5 mM to induce expression of the IFN-γ proteins. The cells were harvested by centrifugation, 3 hours post induction and frozen at −20° C.

Cell pellets were thawed and treated with 10 ml of BPER™ bacterial protein extraction reagent according to the manufacturer's (Pierce) protocols. Other useful methods for lysing the cells include homogenization and use of high pressure. The insoluble or aggregated material, which contains the bulk of the IFN-γ protein, was recovered by centrifugation and resuspended in 10 ml B-PER™. This mixture was next treated with lysozyme (200 µg/ml) for 10 min to further disrupt the cell walls, followed by MgCl$_2$ (10 mM final concentration) and protease-free DNAse (2

µg/ml). Insoluble IFN-γ protein was collected by centrifugation and washed by resuspension in water and recentrifugation.

A variety of conditions for refolding the insoluble protein were tested in an experimental matrix format with wild type IFN-γ and the cysteine variants. Solubilization reagents tested included chaotropic agents such as urea and guanidine in the presence of a reducing agent (dithiothreitol, cysteine or TCEP [Tris (2-carboxyethyl)phosphine-HCl]) and 20 mM Tris, base. For the renaturation step, the solubilizations were diluted 20 fold with a buffered solution which contained one or more of the following additives: glycerol (5-25%), arginine (100-500 mM), Tween 20 (0.1-1%), guanidine (0.1-1 M), urea (0.1-3 M), copper sulfate (40 µmolar), and/or EDTA (1-2 mM). The refolds were left at 4° C. and analyzed by C4 Reversed Phase (RP) HPLC.

The greatest yield of refolded soluble IFN-γ resulted when the insoluble material recovered from the detergent cell break was dissolved in 6 M guanidine, 10 mM TCEP in 20 mM Tris, pH 8.0 where as wild type IFN-γ could be refolded in the absence of a reducing agent while the cysteine muteins required the presence of a reducing agent. Other reducing agents such as cysteine, dithiothreitol, cysteamine, reduced glutathionine, or beta-mercaptoethanol can be substituted for TCEP. This mixture was stirred for 2 hours at room temperature, centrifuged to clarity, and gently diluted 28 fold into the renaturation solution consisting of 0.3 M guanidine, 1 mM TCEP, 1 mM EDTA, and 20 mM Tris, pH 8.0. This refold mixture was allowed to sit at 4° C. overnight without agitation.

Each refold (560 ml) was clarified by centrifugation and diluted 2× with 20 mM Tris, 1 mM TCEP, pH 8.0 (S-Sepharose Buffer A). The mixture was next loaded onto a 10 ml S-Sepharose column (GE Biosciences) equilibrated in Buffer A. The column was eluted with a linear salt gradient (20 column volumes) from 25%-75% Buffer B (Buffer A+1 M NaCl). TCEP was used as the reducing agent in the column buffers because it does not interfere with the PEGylation reaction but does keep the protein from forming disulfide bonds. Alternatively, other reducing agents (cysteine, dithiothreitol, cysteamine, reduced glutathione, beta mercaptoethanol and related compounds) can be included in the column buffers and then subsequently removed by dialysis or chromatography before adding the PEG reagent. If a reducing agent such as cysteine (or cysteamine, dithiothreitol, reduced glutathione, beta mercaptoethanol or a dithiol (e.g., cystine, oxidized glutathione, cystamine) that can form a mixed disulfide when reduced) that is capable of forming a mixed disulfide with the free cysteines in IFN-□□is used in the column buffers or refold and renaturation solutions, an additional reduction step is required before PEGylation.

The S-Sepharose fractions were assayed by SDS-PAGE. It should be noted that when analyzed by SDS-PAGE, IFN-γ runs as a monomer due to the disruption of the hydrophobic interactions that hold the IFN-γ dimer together. Any disulfide-bonded material is reduced due to the presence of TCEP in the S-Sepharose buffers. Fractions with substantially pure IFN-γ were pooled and frozen. Protein concentrations were measured using a Bradford protein assay. Between 20-30 mgs of purified IFN-γ protein (depending on the construct) were typically recovered from a 400 ml shake flask culture.

Example 4. HPLC Assays for Characterization of the Wild Type and IFN-γ Cysteine Variants A Reversed Phase (C4) HPLC method was developed for the purpose of evaluating refold yields and the final purity of the recombinant IFN-γ and the IFN-γ variants. A 50 µl aliquot of sample is applied to a C4 Vydac (or similar C4 HPLC column) previously equilibrated in 60% Buffer A (water+0.1% trifluoroacetic acid (TFA): 40% Buffer B (acetonitrile+0.1% TFA). The column is eluted with a 15 minute linear gradient from 40% Buffer B to 45% Buffer B. Absorbance is monitored at 215 nm. A Beckman System Gold HPLC can be used for these experiments. IFN-γ elutes at approximately 6 minutes.

The purified IFN-γ proteins were also analyzed by Size Exclusion (SEC) HPLC to confirm that the proteins were dimeric. Samples of the proteins were applied to a Bio-Sil SEC 400 (BioRad) HPLC column and eluted with an isocratic gradient of 1.2 M KCl, pH 7.5. BioRad MW standards were used to calibrate the SEC HPLC column. The molecular weights for IFN-γ muteins and wild type IFN-γ were approximately 40 kDa as expected for the homodimer.

Example 5. Amine PEGylation of IFN-γ

Wild type IFN-γ can also be PEGylated using amine reactive PEG reagents. Because the water hydroxyl anion of the aqueous buffer competes with the primary amines, an excess of active PEG is usually needed, on the order of 2 fold to 100 fold depending on the protein's reactivity. The predominant site(s) of PEGylation can be controlled based on the pH of the buffer. Generally, at pH values above 8.0, the epsilon-NH3 groups react first whereas at approximated pH 5-7, alpha-NH2 is the most reactive.

For N-terminal PEGylation, IFN-γ is diluted into a buffer that has sufficient capacity to maintain the pH of the reaction between 5-7. Buffers containing primary amines such as Tris should be avoided. The protein's concentration can be on the order of 0.01 mg-50 mg/mL. PEG is added on the order of 2- to 100-fold excess, preferably 2- to 10-fold excess. The reaction is allow to sit overnight at 4° C. or until the reaction is considered complete. The PEGylated protein is separated from the non-PEGylated protein and the PEG reagents by column chromatography using ion exchange, hydrophobic interaction, or size exclusion chromatography. Chromatography can also be used to separate the PEGylated isoforms of the proteins that vary by the location and/or the number of PEGs attached. The proteins can be visualized by UV absorbance at 280 nm whereas the PEG molecules can be identified by iodine assay (Sims et al., 1980).

For non-specific amine PEGylation the above reaction is run at a pH greater than 8. The number of attachments desired in the final product can be controlled by the amount of excess PEG reagent added and the time that the reaction is allowed to proceed.

Example 6. Thiol Specific PEGylation of IFN-γ Cysteine Muteins

PEGylated IFN-γ can be prepared using a vinylsulfone or maleimide PEG reagents. Thiol specific PEG reagents ranging from 2-60 kDa and linear or branched are available from Nektar (USA), Nippon Oil and Fat (Japan) and Sunbio (South Korea).

Each IFN-γ cysteine mutein (0.5 mg) was diluted in 100 mM Tris, pH 8 to a final concentration of 100 µg/ml. Four aliquots of a 2.5× molar excess of 10 kDa maleimide-PEG were added at 30 min intervals (0, 30 min, 1 hr and 1.5 hr). After two hours at room temperature, the mixture was diluted with an equal volume of the 20 mM Tris, pH 8.0 and loaded onto a 1 ml S-Sepharose column equilibrated in 20 mM Tris, pH 8.0 The PEGylated protein was eluted using a 20-60% gradient of buffer B (20 mM Tris, 1 M NaCl, pH 8.0) over 30 column volumes. The fractions were analyzed by SDS-PAGE. Fractions containing purified diPEG-Cys-IFN-γ (one PEG per monomer) were pooled and analyzed by the Bradford assay to determine the protein concentration. DiPEG-Cys-IFN-γ also is referred to as PEG2-Cys-IFN-γ.

The purified diPEGylated IFN-γ proteins were also analyzed by SEC-HPLC to confirm that the proteins had two PEGs attached and remained dimeric. PEGylation increases a protein's effective molecular weight more than would be expected based on the molecular weight of the PEG moiety due to the water of hydration associated with the PEG group. As mentioned previously, a BioRad Bio-Sil 400 was used for SEC analysis. The column was calibrated using BioRad Gel permeation molecular weight markers. Based on SEC, the purified PEGylated IFN-γ proteins had apparent molecular weights of ~315 kDa as expected for IFN-γ dimer with two 10 kDa PEGs attached. Similar experiments can be used to modify the proteins with different size PEGs (e.g. 20 kDa, 30 kDa, and 40 kDa PEGs, linear or branched).

Example 7. Method for Measuring the Bioactivities of Purified Wild Type IFN-γ and the IFN-γ Cysteine Variants The human ovarian cancer NIH OVCAR-3 cell line (ATCC) is sensitive to the growth inhibiting properties of IFNs and can be used to measure the bioactivities of IFN-α, IFN-β and IFN-γ (Horoszewicz et al., 1979; Evinger and Pestka, 1981; our unpublished results). This assay measures the uptake and bioreduction of the tetrazolium salt MTS [3-(4,5-dimethylthiazol-2-yl)-5-3-carboxymethoxyphenyl)-2-(4-sulphophenyl)-2H-tetrazolium] and is proportional to cell number. In the presence of an electron coupler such as phenazine methosulfate, MTS is converted to a formazan product that is soluble in tissue culture media and can be measured directly at 490 nm (Mosmann 1983). OVCAR cells are adherent cells and maintained in MEM supplemented with 10% FBS, 50 units/ml Pen/Strep, and 2 mM L-glutamine. Cells are passaged every 4 days in 1:2 dilutions.

For the bioassay, fifty μl ($5 \times 10^3$ cells) of the cell suspension were aliquoted per test well of a flat bottom 96 well tissue culture plate. Control wells contained media but no cells. Serial dilutions for the protein samples and standard (IFN-γ, Endogen) were prepared in assay media. Fifty μl of the diluted protein samples were added to the test wells in triplicate and the plates were incubated at 37° C. in a humidified 5% $CO_2$ tissue culture incubator for ~7 days. On the 7th day, the media is removed and the wells washed with PBS. 100 μl of phenol red free media is added back to the wells along with 20 μl of an MTS/PMS mixture (CellTiter 96 Aqueous One Solution, Promega). Alternatively, the MTS/PMS solution can be added directly to the test wells without washing. The plates are incubated again at 37° C. in the tissue culture incubator for 1-4 h. The plates are read at an absorbance of 490 nm using a microplate reader. Mean absorbance values for the triplicate control wells were subtracted from mean values obtained for the test wells. An $IC_{50}$, the concentration at half maximal inhibition, was calculated for each sample to compare bioactivities of the proteins. The IFN-γ cysteine variants, and PEGylated forms of IFN-γ were assayed as described above. Ave $IC_{50}$ values are shown in Table 2.

TABLE 2

Bioactivity and Yield Data for IFN-γ cysteine variants and PEGylated IFN-γ cysteine variants

| IFN-γ Construct | Region of Protein with Cysteine Mutation | Mean IC50s ± SD (ng/ml) (n ≥ 2) | Activity relative to Wild Type | PEGylation Efficiency (%) | Mean IC50s of PEG protein (ng/ml) (n ≥ 2) | Activity relative to Wild Type |
|---|---|---|---|---|---|---|
| Wild type[1] | — | 81 ± 53 | 1.0 | — | — | — |
| Wild type[2] | — | 35 ± 7 | 2.2 | — | — | — |
| E38C | B-C loop | 90 ± 14 | 0.9 | 67 | 70 ± 42 | 1.1 |
| E39C | B-C loop | 30 | 2.7 | 47 | 130 ± 99 | 0.6 |
| S40C | B-C loop | 250 ± 212 | 0.3 | 55 | 425 ± 189 | 0.2 |
| D63C | C-D loop | 200 | 0.4 | 50 | 85 ± 21 | 0.9 |
| Q64C | C-D loop | 55 ± 21 | 1.5 | 95 | 40 ± 14 | 2.0 |
| S65C | C-D loop | 90 ± 14 | 0.9 | 95 | 30 | 2.7 |
| I66C | C-D loop | 250 ± 71 | 0.3 | <20 | 400 ± 14 | 0.2 |
| S84C | D-E loop | 75 ± 21 | 1.1 | 68 | 75 ± 35 | 1.1 |
| N85C | D-E loop | 250 ± 71 | 0.3 | 66 | 90 ± 14 | 0.9 |
| K86C | D-E loop | 300 | 0.3 | 73 | 85 ± 21 | 1.0 |
| N97C | Helix E | 80 | 1.0 | 40 | 95 ± 7 | 0.9 |
| V99C | E-F loop | 250 ± 71 | 0.3 | 20 | 400 ± 141 | 0.2 |
| V100C | E-F loop | 350 ± 71 | 0.2 | 30 | 400 | 0.2 |
| T101C | E-F loop | 55 ± 7 | 1.4 | 50 | 25 ± 7 | 3.2 |
| D102C | E-F loop | 200 | 0.4 | 50 | 85 ± 21 | 1.0 |
| L103C | E-F loop | 45 ± 21 | 1.8 | 50 | 9 | 9 |

[1]Purchased from Endogen (Pierce Biotech)
[2]Prepared in-house

In vitro bioactivities of certain IFN gamma muteins (N25C, K37C, Q67C, N83C and a mutein in which Q1 is deleted) were measured using the human ovarian cancer CAOV-3 cell line, which is available from the American Type Culture collection (Manassas, Va.; cat # HTB-75). The cells were maintained in DMEM media supplemented with 10% fetal bovine serum, penicillin, streptomycin and Glutamax. For the bioassay, fifty μl ($5 \times 10^3$ cells) of the cell suspension were aliquoted per test well of a flat bottom 96 well tissue culture plate. Control wells contained media but no cells. Serial dilutions for the protein samples and a WT IFN-gamma standard were prepared in assay media (phenol red-free DMEM media supplemented with 10% fetal bovine serum, 50 units/mL penicillin, 50 micrograms/mL streptomycin and 2 mM Glutamax. Fifty µl of the diluted protein samples were added to the test wells in triplicate and the plates were incubated at 37° C. in a humidified 5% $CO_2$ tissue culture incubator for 4 days. On day 4, 20 µl of CellTiter 96 Aqueous One Solution (Promega) was added to each well and the plates incubated at 37° C. in the tissue culture incubator for 1-4 h. The plates are read at an absorbance of 490 nm using a microplate reader. Mean absorbance values for the triplicate control wells were subtracted from mean values obtained for the test wells. $IC_{50}$ values were calculated for each protein and are shown in Table 3. The data indicate that in vitro bioactivities of the muteins were comparable to that of wild type IFN gamma. $IC_{50}$s for the proteins were within 2-fold of the $IC_{50}$ for wild type IFN gamma. Q1 is thought to be important for biological activity of interferon gamma; thus it was unexpected to find that a mutant lacking Q1 had similar biological activity as wild type interferon gamma.

TABLE 3

$IC_{50}$s of IFN gamma muteins for inhibiting growth of human CAOV-3 cells in vitro.

| IFN Gamma Mutein | Region of Protein with Cysteine Mutation | $IC_{50}$ (ng/mL) |
| --- | --- | --- |
| WT IFN gamma | — | 1.4 ± 0.7 |
| Q1 deletion | — | 0.7 ± 0.2 |
| N25C | A-B loop | 2.2 ± 0.5 |
| K37C | B-C loop | 0.8 ± 0.2 |
| Q67C | C-D loop | 2.3 ± 0.1 |
| N83C | D-E loop | 1.5 ± 0.5 |

Example 8. Pharmacokinetic Experiments to Demonstrate Increased Circulating Half-lives of PEG2-Cys-IFN-γ Relative to unPEGylated IFN-γ

Rats (3/group) were given a single intravenous (IV) injection (100 µg/kg) of wild type IFN-γ or 10 kDa PEG2-Cys-IFN-γ (S84C). Blood samples are drawn at various times and frozen. A commercially available IFN-γ ELISA kit (R&D systems) was used to measure serum levels of the IFN-γ proteins. Alternatively, quantitative Westerns blots can be run to determine serum levels. Terminal pharmacokinetic parameters were calculated using WinNonlan software and non-compartmental analysis. The circulating half-lives were calculated to be 1.2 hr for wild type IFN-γ and 9.5 hr for 10 kDa PEG2-Cys-IFN-γ (S84C). These data indicate that the half-lives of the PEGylated proteins were much longer than the half-life of wild type IFN gamma.

In an analogous experiment, rats (3/group) were given single a intraperitoneal (ip) injection of wild type IFN-γ, 10 kDa PEG2-Cys-IFN-γ (L103C), 20 kDa PEG2-Cys-IFN-γ (L103C) or 40 kDa PEG2-Cys-IFN-γ (L103C). Blood samples were drawn at various times and analyzed by the ELISA assay. The circulating half-lives were calculated to be <1 hr for wild type IFN-γ, 10.3 hr for 10 kDa PEG2-Cys-IFN-γ, 17.1 hr for 20 kDa PEG2-Cys-IFN-γ and 21.7 hr for 40 kDa PEG2-Cys-IFN-γ. These data indicate that the half-lives of the PEGylated proteins were much longer than the half-life of wild type IFN gamma.

Example 9. Evaluation of PEGylated IFN-γ's in Vivo Activity in Xenograft Tumor Model The relative efficacies of the PEGylated IFN-γ variants as an anti-tumor drug can be evaluated in a human tumor xenograft growth using human tumor cell lines, such as NIH-OVCAR-3 cells. in athymic nude mice (Burke et al., 1999, Malik et al., 1991). Inhibition of human tumor xenograft growth in nude mice occurs through a direct antiproliferative effect on the human tumor cells. Since these mice cannot mount an immune response, potential immunogenicity problems resulting from use of human IFN-γ proteins in mice will not be an issue.

Athymic nude mice can be purchased from a commercial vendor such as Charles River Laboratories. Each mouse is injected intraperitoneally or subcutaneously with $1-5 \times 10^6$ NIH-OVCAR-3 tumor cells on day 0 and randomly assigned to test groups, consisting of ten mice each. Seven days later the different test groups receive ip, sc or iv injections of human wild type IFN-γ, PEG2-Cys-IFN-γ or placebo (vehicle solution) at specified intervals: every day (ED), every other day (EOD) or every third day (ETD) for 8-10 weeks. Doses of the proteins required for tumor growth inhibition can be determined experimentally and are expected to be in the range of 5 µg/mouse/injection to 5 mg/mouse/injection. Tumor volumes in the test groups are measured over time. At time of sacrifice, autopsies are performed to evaluate tumor burden and tumor weight. We expect that the tumors in the animals treated with PEG2-Cys-IFN-γ will be smaller than the placebo and wild type IFN-γ groups.

We compared the ability of IFN-gamma and the 40 kDa-PEG-L103C protein to inhibit growth of human NIH: OVCAR-3 tumor cells transplanted into athymic nude mice. Female athymic nude (nu/nu) mice were obtained from Charles River (Wilmington, Mass.). The NIH:OVCAR-3 cells were grown in vitro, harvested by trypsinization, washed and resuspended at a concentration of $25 \times 10^6$ cells per mL in a 50:50 mixture of MEM media/Matrigel. Matrigel was purchased from BD Biosciences (Bedford, Mass.). Animals were randomized to different test groups according to body weight on Day 0. Mice (10/group) received subcutaneous injections of 0.2 mL of the MEM media/Matrigel mixture containing $5 \times 10^6$ cells in the axillary area on Day 0. Animals received subcutaneous injections (0.2 mL/animal) of the test compounds beginning on Day 1 and continuing through Day 70 using a 3×/week dosing schedule (Monday, Wednesday, Friday). Mice were weighed on Day 0, prior to the injection of cells, and on the days of tumor measurements. Tumors were measured weekly using calipers for 10 weeks post injection. Tumor volume was determined using a formula of ((width×width)×length)/2). The different treatment groups received injections of vehicle solution [phosphate buffered saline containing 0.1 mg/mL of mouse albumin (Sigma-Aldrich, Inc., St. Louis, Mo.)], wild type IFN-gamma in vehicle solution (15 µg/injection/mouse) or 40 kDa-PEG-L103C in vehicle solution (15 µg/injection/ mouse). Wild type IFN-gamma was prepared by us.

Final tumor volumes and weights at necropsy (on day 70) are summarized in Table 4. Mean tumor volumes of animals treated with wild type IFN-gamma were, on average, larger than tumors in animals treated with vehicle solution, indicating that there is no benefit of wild type IFN-gamma versus placebo for inhibiting tumor growth at this dose and dosing frequency. Final mean tumor volumes in animals treated with wild type IFN-gamma and vehicle solution were not statistically different from one another. In contrast, mean tumor volumes in animals treated with PEG-L103C were 51% smaller than mean tumor volumes in animals treated with vehicle solution and 68% smaller than mean tumor volumes in animals treated with wild type IFN-gamma. The differences between mean tumor volumes in animals receiving PEG-L103C and vehicle or wild type IFN-gamma were statistically significant (p<0.01). Mean tumor weights at necropsy (Day 70) were significantly reduced in animals receiving PEG-L03C compared to mean tumor weights in animals receiving injections of vehicle solution (53% reduction) or wild type IFN-gamma (69% reduction).

TABLE 4

Tumor volumes and weights in mice treated with Vehicle, wild type IFN-gamma and PEG-L103C at study termination on day 70. Data are means ± SD for 10 mice per group.

| Compound | Tumor Volume (mm$^3$) | Tumor Weight (g) |
|---|---|---|
| 1. Vehicle | 949 ± 139 | 0.939 ± 0.136 |
| 2. WT IFN-gamma | 1,475 ± 280 | 1.424 ± 0.280 |
| 3. PEG-L103C | 466 ± 89 * | 0.444 ± 0.063 * |

* p < 0.01 vs Vehicle and wild type IFN-gamma

Example 10. Evaluation of PEGylated IFN-γ's in Vivo Activity at Stimulating the Immune System in Vivo The efficacy of PEG2-Cys-IFN-γ as an anti-infective drug, can also be tested in a mouse model of chronic granulomatous disease (CGD). A mouse knockout model of CGD has been developed by Jackson et al. (1995) that has a targeted disruption of the p47phox gene. Identical to human CGD, leukocytes from p47phox−/− mice produce no superoxide and are unable to kill staphylococci efficiently. The p47phox−/− mice develop lethal infections and granulomatous inflammation similar to those encountered in human CGD patients. Researchers have investigated the prophylactic effect of IFN-γ in the CGD mouse model p47phox form of CGD. In an animal study, murine IFN-γ, (20,000 U) or placebo was administered subcutaneously to p47phox−/− mice. By 6 weeks of study, there were 3 infections in the IFN-γ treated group (n=60) as compared with 13 infections in the placebo group (n=58) (77% reduction in infections, p<0.01).

For this study, it is necessary to prepare the murine version of a PEG-IFN-γ cysteine mutein since there is no cross-reactivity between species. Murine IFN-γ is commonly used in mouse models of infectious diseases (Jackson et al., 2001; Murray, 1990; Flynn et al., 1993).

Like its human counterpart, murine IFN-γ exists as a glycosylated noncovalent homodimer with similar secondary and tertiary structures. Therefore, it is relatively straightforward to transfer the thiol specific PEGylation technology from the human protein to the mouse protein. FIG. 3 of Ealick et al. (1993) shows the alignment of the human and mouse gamma interferon amino acid sequences, which can be used to choose appropriate mouse amino acids to change to cysteine residues. Murine-human IFN-γ hybrids have been made to identify the regions that are responsible for species specificity recognition of human IFN-γ with the human IFN-γ receptor (Lundell et al., 1994). In particular, it appears that amino acids in the A-B loop (more specifically residues 20-23) and His 111 in Helix F play critical roles in species specific receptor interactions. Several papers describe the expression, refolding and purification of murine IFN-γ (Nagata et al., 1886; Zavodny et al., 1988; Lundell et al., 1994). The amino acid sequence of murine IFN-γ is given in Sequence ID No. 2. When expressed in E. Coli, the protein may contain an N-terminal methionine not found in the native protein. Mouse IFN gamma contains a C-terminal cysteine residue. This cysteine residue can be deleted or substituted with another amino acid, preferably, alanine, serine or threonine, to facilitate expressions and purification of the protein.

The specific PEG2-Cys-IFN-γ to be used for these experiments (10, 20, or 40 kDa PEG) can be determined by the results of the rat PK experiments described above and their relative activities in the in vitro bioassay. The knockout mice are commercially available from Taconic (Albany, N.Y.) in collaboration with the National Institute of Allergy and Infectious diseases (NIAD) exchange program. Before the study begins the animals are maintained on a broad-spectrum antibiotic. At the initiation of the experiment, the antibiotics are removed from their water, making them susceptible to infection. The animals are monitored three times weekly for gross evidence of infection for three months.

Example 11. Evaluation of PEGylated IFN-γ's in Vivo Activity at Inhibiting Viral Infections The ability of PEG$_2$-Cys-IFN-γ proteins to inhibit viral replication can be determined using in vitro viral assays. The bioactivities of the cysteine muteins and the PEG2-Cys-IFN-γ proteins can be measured using an in vitro viral cytopathic effect inhibition assay (Arakawa et al., 1985). Human HEp2 or WISH cells (ATCC) are plated in 96-well plates (3×10$^4$ cells/well) and grown to near confluency at 37° C. The cells are washed and treated for 24 hr with serial dilutions of the test proteins. Controls include no IFN-γ, wild type IFN-γ prepared by us and wild type IFN-γ purchased from a commercial vendor. Encephalomyocarditis virus (EMCV) is added at a multiplicity of infection of 0.1 and the plates incubated for a further 24-48 hr at 37° C. Additional controls include samples without virus. When 90% or more of the cells have been killed in the virus-treated, no IFN-γ control wells (determined by visual inspection of the wells), an MTS solution is added to the wells. Absorbance of the wells is read at 490 nm after 1-4 hr. Samples are normally analyzed in triplicate. IC$_{50}$ values can be used to compare the relative potencies of the PEG$_2$-Cys-IFN-γ cysteine muteins. The IC$_{50}$ value for commercially available IFN-γ in this assay is typically between 0.05-0.15 ng/ml.

Example 12. Glucagon

Glucagon is a small peptide that is secreted by intestinal cells and acts primarily on the liver to stimulate glucose production and secretion. Glucagon is important for counteracting hypoglycemia. The amino acid sequence of glucagon is represented herein by SEQ ID NO:8. A cysteine residue can be added preceding the first amino acid, H1, or following the last amino acid T29. A cysteine residue also can be introduced into the protein by substitution for at least one amino acid selected from the group consisting of H1, S2, Q3, G4, T5, F6, T7, S8, D9, Y10, S11, K12, Y13, L14, D15, S16, R17, R18, A19, Q20, D21, F22, V23, Q24, W25, L26, M27, N28, T29. These amino acid changes can be made in the context of native sequence glucagons or in the context of glucagon analogs, such as those described in U.S. Pat. No. 5,510,459. The cysteine variants of the present invention can be modified with cysteine-reactive moieties such as cysteine reactive PEGs. The cysteine-modified peptides can be purified from unmodified peptides by any of a number of methods known in the art such as column chromatography.

Alternatively, glucagon can be modified with PEG at K12 using an amine-reactive PEG reagent. Alternatively, K12, can be changed to a non-lysine residue, preferably arginine, and a new lysine residue introduced into the protein. An amine-reactive PEG can then be attached to the added lysine residue. The added lysine residue can be inserted preceding the first amino acid, H1, or following the last amino acid T29. A lysine residue also can be added to the protein by substitution for at least one amino acid selected from the group consisting of H1, S2, Q3, G4, T5, F6, T7, S8, D9, Y10, S11, Y13, L14, D15, S16, R17, R18, A19, Q20, D21, F22, V23, Q24, W25, L26, M27, N28, T29. These amino acids can be made in the context of native sequence glucagons or in the context of glucagon analogs, such as those described in U.S. Pat. No. 5,510,459. The lysine variants of the present invention can be modified with amine-reactive moieties such as amine-reactive PEGs. The amine-modified peptides can be purified from unmodified peptides by any of a number of methods known in the art such as column chromatography.

Glucagon also can be modified at its N-terminus using amine-reactive moieties using methods well known in the art.

The modified glucagon proteins can be tested for in vitro and in vivo biological activity using methods known in the art.

Example 12. GLP-1

Glucagon-like peptide-1 (GLP-1) is a 31 amino acid peptide synthesized primarily by the L-cells of the intestine in response to nutrient ingestion. The protein also exists as a 30 amino acid form, called the amide form, in which G31 is absent. The protein is expressed as part of a larger polypeptide, proglucagon, that is proteolytically cleaved to yield GLP-1, glucagon, oxyntomodulin (OXCM) and glucagon-like peptide-2 (GLP-2), and several additional peptides. The amino acid sequence of GLP-1 is conserved among mammals. GLP-1 has several properties that suggest it may prove useful for treating diabetes and obesity. GLP-1 acts on the pancreas to stimulate proinsulin gene expression, insulin secretion and inhibit glucagon secretion. These effects of GLP-1 are glucose-dependent; thus GLP-1 may provide a safe mechanism for lowering elevated blood glucose levels such as is seen in diabetes. GLP-1 also stimulates growth and proliferation of pancreatic beta cells, which are the pancreatic cells responsible for synthesizing insulin. Thus, GLP-1 could be used to increase beta cell mass or increase insulin secretion potential in patients with diabetes. GLP-1 also reduces caloric intake, reduces hunger sensations, and slows gastric emptying and acid secretion, suggesting that it may prove useful as an anti-obesity drug. Since many type 2 diabetics are obese, GLP-1 could provide a dual mechanism for improving the physiology of these patients, both by decreasing weight and improving their ability to synthesize and utilize insulin.

The amino acid sequence of GLP-1 is represented herein by SEQ ID NO:9. A cysteine residue can be added preceding the first amino acid, H1, or following the last amino acid G31. A cysteine residue also can be introduced into the protein by substitution for at least one amino acid selected from the group consisting of H1, A2, E3, G4, T5, F6, T7, S8, D9, V10, S11, S12, Y13, L14, E15, G16, Q17, A18, A19, K20, E21, F22, I23, A24, W25, L26, V27, K28, G29, R30 and G31. These amino acid changes can be made in the context of the 1-30 amino acid form of GLP-1 or the 1-31 amino acid form of GLP-1. These amino acids can be made in the context of GLP-1 analogs, such as those described in U.S. Pat. Nos. 6,458,924, 6,620,910, 6,703,365, 7,041,646, 7,067,488, 7,101,843, 7,138,486, 7,199,217, and 7,211,557.

A preferred GLP-1 analog is one that inhibits cleavage of H1 and A2 from the peptide by proteases. A preferred GLP-1 analog is one in which A2 is changed to a non-alanine amino acid, preferably serine, glycine or cysteine. Another preferred GLP-1 analog is one in which E3 is substituted with an a non-glutamic acid amino acid such as proline, which prevents proteolytic cleavage of H1 and A2 from the peptide. The cysteine variants of the present invention can be modified with cysteine-reactive moieties such as cysteine reactive PEGs. The cysteine-modified peptides can be purified from unmodified peptides by any of a number of methods known in the art such as column chromatography.

Alternatively, GLP-1 can be modified with PEG at one or both of the lysine residues K20 and K28. To make the PEG reaction specific for a particular lysine residue, K20 or K28 can be changed to a non-lysine amino acid, preferably arginine, and the mutant protein modified with PEG at the remaining lysine residue. Additionally, both lysine residues, K20 and K28, can be changed to non-lysine residues and a new lysine residue introduced into the protein. The new lysine residue can be added preceding the first amino acid, H1, or following the last amino acid G31. A lysine residue also can be introduced into the protein by substitution for at least one amino acid selected from the group consisting of H1, A2, E3, G4, T5, F6, T7, S8, D9, V10, S11, S12, Y13, L14, E15, G16, Q17, A18, A19, E21, F22, I23, A24, W25, L26, V27, G29, R30 and G31. These amino acid changes can be made in the context of the 1-30 amino acid form of GLP-1 or the 1-31 amino acid form of GLP-1. These amino acids can be made in the context of GLP-1 analogs, such as those described in the preceding paragraph. The lysine variants of the present invention can be modified with amine-reactive moieties such as amine-reactive PEGs. The amine-modified peptides can be purified from unmodified peptides by any of a number of methods known in the art such as column chromatography.

GLP-1 also can be modified at its N-terminus using methods described in the art. The modified GLP-1 proteins can be tested for in vitro and in vivo biological activity using methods well known in the art.

Example 13. GLP-2

GLP-2 is a small peptide secreted by intestinal cells. GLP-2 acts locally within the intestine to stimulate intestinal crypt cell proliferation, inhibit intestinal cell apoptosis and expand the mucosal epithelium. GLP-2 also promotes nutrient absorption. The amino acid sequence of GLP-2 is represented herein by SEQ ID NO:10. A cysteine residue can be added preceding the first amino acid, H1, or following the last amino acid D33. A cysteine residue also can be introduced into the protein by substitution for at least one amino acid selected from the group consisting of H1, A2, D3, G4, S5, F6, S7, D8, E9, M10, N11, T12, I13, L14, D15, N16, L17, A18, A19, R20, D21, F22, I23, N24, W25, L26, I27, Q28, T29, K30, I31, T32, and D33. These amino acids can be made in the context of native sequence GLP-2 or in the context of GLP-2 analogs, such as those described in U.S. Pat. Nos. 7,112,567, 7,056,886, and 5,952,301. A preferred GLP-3 analog is one that inhibits cleavage of H1 and A2 from the peptide by proteases. A preferred GLP-2 analog is one in which A2 is changed to a non-alanine amino acid, preferably serine, glycine or cysteine. Another preferred GLP-2 analog is one in which D3 is substituted with a non-aspartic acid amino acid such as proline, which prevents proteolytic cleavage of H1 and A2 from the peptide. The cysteine variants of the present invention can be modified with cysteine-reactive moieties such as cysteine reactive PEGs. The cysteine-modified peptides can be purified from unmodified peptides by any of a number of methods known in the art such as column chromatography.

Alternatively, GLP-1 can be modified with an amine-reactive moiety at K30. Alternatively, K30, can be changed to a non-lysine residue, preferably arginine, and a new lysine residue introduced into the protein. An amine-reactive moiety can then be attached to the newly added lysine residue. The new lysine residue can be inserted preceding the first amino acid, H1 or following the last amino acid D33. A lysine residue also can be added to the protein by substitution for at least one amino acid selected from the group consisting of H1, A2, D3, G4, S5, F6, S7, D8, E9, M10, N11, T12, I13, L14, D15, N16, L17, A18, A19, R20, D21, F22, I23, N24, W25, L26, I27, Q28, T29, I31, T32, D33. These amino acids can be made in the context of native sequence GLP-2 or GLP-2 analogs, such as those described in U.S. Pat. Nos. 7,112,567, 7,056,886, and 5,952,301. A preferred GLP-2 analog is one in which A2 is changed to a non-alanine amino acid, preferably serine or glycine. The lysine variants of the present invention can be modified with amine-reactive moieties such as amine-reactive PEGs. The amine-modified peptides can be purified from unmodified peptides by any of a number of methods known in the art such as column chromatography.

GLP-2 also can be modified at its N-terminus using methods well known in the art. The modified GLP-2 proteins can be tested for in vitro and in vivo biological activity using methods well known in the art.

Example 14. Exendin-4

The amino acid sequence of exendin-4 is represented herein by SEQ ID NO:11. Exendin is a GLP-1 agonist and exerts similar functions as GLP-1. A cysteine residue can be inserted preceding the first amino acid, H1, or following the last amino acid S38. A cysteine residue also can be introduced into the protein by substitution for at least one amino acid selected from the group consisting of H1, G2, E3, G4, T5, F6, T7, S8, D9, L10, S11, K12, Q13, M14, E15, E16, E17, A18, V19, R20, L21, F22, I23, E24, W25, L26, K27, N28, G29, G30, P31, S32, S33, G34, A35, P36, P37, P38, and S39. These amino acids can be made in the context of native sequence exendin-4 of exendin-4 analogs, such as those described in U.S. Pat. Nos. 6,767,887, 6,924,264, 7,115,569, 7,153,825, and 7,157,555. The cysteine variants of the present invention can be modified with cysteine-reactive moieties such as cysteine reactive PEGs. The cysteine-modified peptides can be purified from unmodified peptides by any of a number of methods known in the art such as column chromatography.

Alternatively, exendin-4 can be modified with an amine-reactive moiety at one or both of the lysine residues K12 and K27. To make the reaction specific for a particular lysine residue, K12 or K27 can be changed to a non-lysine amino acid, preferably arginine, and the mutant protein modified with an amine-reactive moiety at the remaining lysine residue. Additionally, both lysine residues, K12 and K27, can be changed to non-lysine residues, preferably arginine residues, and a new lysine residue introduced elsewhere in the protein. The new lysine residue can be added preceding the first amino acid, H1, or following the last amino acid S38. A lysine residue also can be introduced into the protein by substitution for at least one amino acid selected from the group consisting of H1, G2, E3, G4, T5, F6, T7, S8, D9, L10, S11, Q13, M14, E15, E16, E17, A18, V19, R20, L21, F22, I23, E24, W25, L26, N28, G29, G30, P31, S32, S33, G34, A35, P36, P37, P38, and S39. These amino acid changes can be made in the context of native sequence exendin-4 or in the context of exendin-4 analogs, such as those described in U.S. Pat. Nos. 6,767,887, 6,924,264, 7,115,569, 7,153,825, and 7,157,555. The lysine variants of the present invention can be modified with amine-reactive moieties such as amine-reactive PEGs. The amine-modified peptides can be purified from unmodified peptides by any of a number of methods known in the art such as column chromatography.

Exendin-4 also can be modified at its N-terminus using methods described in the art. The modified exendin-4 proteins can be tested for in vitro and in vivo biological activity using methods known in the art.

Example 15. PYY

Peptide YY (PYY) is a small peptide secreted by the intestine. PYY functions to control food intake. The amino acid sequences of human PYY is represented herein by SEQ ID NO:12. A truncated form of PYY in which amino acids 1 and 2 are deleted is referred to as PYY 3-36. An alternative form of PYY includes a P at position 34 (P34). A cysteine residue can be added preceding the first amino acid, Y1, or following the last amino acid Y36. A cysteine residue can be added preceding the first amino acid, I3, of the PYY 3-36 form of the peptide. A cysteine residue also can be introduced into the protein by substitution for at least one amino acid selected from the group consisting of Y1, P2, I3, K4, P5, E6, A7, P8, G9, E10, D11, A12, S13, P14, E15, E16, L17, N18, R19, Y20, Y21, A22, S23, L24, R25, H26, Y27, L28, N29, L30, V31, T32, R33, Q34, R35, and Y36. These amino acids can be made in the context of native sequence PYY or PYY 3-36 or in the context of PYY or PYY 3-36 analogs such as those described in U.S. Pat. Nos. 6,046,167, 5,328,899, 5,026,685, and 7,186,692. The cysteine variants of the present invention can be modified with cysteine-reactive moieties such as cysteine reactive PEGs. The cysteine-modified peptides can be purified from unmodified peptides by any of a number of methods known in the art such as column chromatography.

PYY also can be modified with an amine-reactive moiety at the N-terminal Y1 amino acid or at the K4 amino acid. Alternatively, K4 can be changed to a non-lysine amino acid, preferably arginine, and a new lysine residue introduced into the protein. The new lysine residue can be added preceding the first amino acid, Y1, or following the last amino acid Y31. A lysine residue also can be introduced into the protein by substitution for at least one amino acid selected from the group consisting of Y1, P2, I3, P5, E6, A7, P8, G9, E10, D11, A12, S13, P14, E15, E16, L17, N18, R19, Y20, Y21, A22, S23, L24, R25, H26, Y27, L28, N29, L30, V31, T32, R33, Q34, R35, and Y36. These amino acids can be made in the context of native sequence PYY or PYY 3-36 or in the context of PYY or PYY 3-36 analogs, such as those described in U.S. Pat. Nos. 6,046,167, 5,328,899, 5,026,685, and 7,186,692. The lysine variants of the present invention can be modified with amine-reactive moieties such as amine-reactive PEGs. The amine-modified peptides can be purified from unmodified peptides by any of a number of methods known in the art such as column chromatography.

PYY or PYY 3-36 also can be modified at its N-terminus using methods described in the art. The modified PYY and PYY 3-36 peptides can be tested for in vitro and in vivo biological activity using methods well known in the art.

Example 16. Ghrelin

Ghrelin is a 28 amino acid peptide that was originally isolated from the stomach. The amino acid sequence of Ghrelin is represented herein by SEQ ID NO:13. Ghrelin circulates in the body in both an acylated form (AC-ghrelin) and a non-acylated (NA-ghrelin) form, with the non-acylated form predominating under most situations. AC-ghrelin has an n-octanoic fatty acid attached to the hydroxyl group of Ser3. AC-ghrelin binds a G protein coupled receptor, GHSR1a, which is preferentially expressed in the pituitary and hypothalamus and is distinct from the growth hormone releasing factor receptor. The GHSR1a receptor also is expressed in a variety of tissues, including adrenal and thyroid gland, heart, liver, kidney and skeletal muscle. NA-ghrelin can bind a different uncharacterized receptor that is expressed in heart muscle and certain other tissues. AC-ghrelin is a naturally occurring growth hormone (GH) secretagogue. Administration of the AC-ghrelin to animals and humans increases circulating GH, prolactin, ACTH and cortisol levels, decreases serum insulin levels, increases plasma glucose levels, in causes hyperglycemia. NA-ghrelin does not cause these changes. NA-ghrelin appears to inhibit the endocrine functions of ghrelin, but not the neuroendocrine functions of AC-ghrelin. NA-ghrelin inhibits the appetite-stimulating effects of AC-ghrelin in humans. NA-ghrelin also inhibits apoptosis of cardiac mycotyes. Both AC-ghrelin and NA-ghrelin share certain functions such as cardiovascular actions, and may be useful for treating heart disease. Both AC-ghrelin and NA-ghrelin inhibit cell death in cardiomyocytes and endothelial cells, and both peptides stimulate proliferation of osteoblast cell lines in vitro. NA-ghrelin has the potential to function as an anti-obesity drug in people. NA-ghrelin also slows emptying of gastric contents. AC-ghrelin stimulates appetite in people and may prove useful for treating metabolic and eating disorders such as cachexia and anorexia. Ghrelin secretion is stimulated by fasting and energy restriction, and inhibited by food intake, glucose, insulin and somatostatin. Ghrlein levels are increased in anorexia and cachexia and decreased in obesity.

In short term studies mice treated with NA-ghrelin decreased food intake and slowed the rate of gastric emptying. These physiological changes were mediated through NA-ghrelin action on the hypothalamus. Thus, NA-ghrelin appears to cause a negative energy balance in the body. Transgenic mice overexpressing NA-ghrelin displayed decreased linear growth, lower food intake, and decreased body weight. These mice displayed lower serum IGF-I and GH levels compared to control mice. NA-ghrelin transgenic mice responded to GHRH but displayed a blunted response to AC-ghrelin administration, suggesting that NA-ghrelin can function as a specific AC-ghrelin antagonist. NA-ghrelin transgenic mice still responded normally to GH releasing hormone, indicating that the antagonist effect was specific for AC-ghrelin and not all GH releasing hormones.

Ghrelin has a circulating half-life of 27-31 min following intravenous administration to humans. AC-ghrelin has a shorter half-life of 9-13 min, possibly due to more rapid degradation.

A cysteine residue can be inserted preceding the first amino acid, G1, or following the last amino acid R28 of ghrelin. A cysteine residue also can be introduced into the protein by substitution for at least one amino acid selected from the group consisting of G1, S2, S3, F4, L5, S6, P7, E8, H9, Q10, R11, V12, Q13, Q14, R15, K16, E17, S18, K19, K20, P21, P22, A23, K24, L25, Q26, P27, and R28. These amino acids can be made in the context of acylated or nonacylated ghrelin. These amino acid changes can be made in the context of ghrelin analogs, such as those described in U.S. Pat. Nos. 7,176,292, 7,115,767, 7,074,562 and 6,967,237. The cysteine variants of the present invention can be modified with cysteine-reactive moieties such as cysteine reactive PEGs. The cysteine-modified peptides can be purified from unmodified peptides by any of a number of methods known in the art such as column chromatography.

Alternatively, Ghrelin can be modified with an amine-reactive moiety at the N-terminus or at one or all of the lysine residues K16, K19, K20 and K24. To make the modification reaction specific for a particular lysine residue, K16, K19, K20 or K24 can be changed to a non-lysine amino acid, preferably arginine, and the mutant protein modified with an amine-reactive moiety at the remaining lysine residue. Additionally, all of the lysine residues, K16, K19, K20 and K24, can be changed to non-lysine residues, preferably arginine residues, and a new lysine residue introduced into the protein. The new lysine residue can be added preceding the first amino acid, G1, or following the last amino acid R28. A lysine residue also can be introduced into the protein by substitution for at least one amino acid selected from the group consisting of G1, S2, S3, F4, L5, S6, P7, E8, H9, Q10, R11, V12, Q13, Q14, R15, E17, S18, P21, P22, A23, L25, Q26, P27, and R28. These amino acids can be made in the context of other Ghrelin analogs, such as those described in U.S. Pat. Nos. 7,176,292, 7,115,767, 7,074,562 and 6,967,237. The lysine variants of the present invention can be modified with amine-reactive moieties such as amine-reactive PEGs. The amine-modified peptides can be purified from unmodified peptides by any of a number of methods known in the art such as column chromatography.

Ghrelin also can be modified at its N-terminus using methods described in the art. The modified ghrelin proteins can be tested for in vitro and in vivo biological activity using methods well known in the art.

Example 17. Oxyntomodulin

Oxyntomodulin (OXM) is a small peptide secreted by the L cells of the intestine. OXM serves to decrease food intake and decrease weight gain, and thus may prove useful for treating obesity. The amino acid sequence of OXM is represented herein by SEQ ID NO:14. OXM is a derivative of glucagon in which the sequence DTKRNKNNIA (SEQ ID NO:15) is added to the first 27 amino acids of glucagon. A cysteine residue can be added preceding the first amino acid, H1, or following the last amino acid A38. A cysteine residue also can be introduced into the protein by substitution for at least one amino acid selected from the group consisting of H1, S2, Q3, G4, T5, F6, T7, S8, D9, Y10, S11, K12, Y13, L14, D15, S16, R17, R18, A19, Q20, D21, F22, V23, Q24, W25, L26, M27, N28, D29, T30, K31, R32, N33, K34, N35, N36, I37, A38. These amino acids can be made in the context of native sequence OXM or OXM analogs such as those described in U.S. Pat. No. 5,858,975. The cysteine variants of the present invention can be modified with cysteine-reactive moieties such as cysteine reactive PEGs. The cysteine-modified peptides can be purified from unmodified peptides by any of a number of methods known in the art such as column chromatography.

Alternatively, OXM can be modified with an amine-reactive moiety at its n-terminus or at one or all of the lysine residues K12, K31, and K34. To make the modification reaction specific for a particular lysine residue, K12, K31 or K34 can be changed to a non-lysine amino acid, preferably arginine, and the mutant protein modified with an amine-reactive moiety at the remaining lysine residue. Additionally, all of the lysine residues, K12, K31, and K34, can be changed to non-lysine residues, preferably arginine residues, and a new lysine residue introduced into the protein. The new lysine residue can be added preceding the first amino acid, H1, or following the last amino acid A38. A lysine residue also can be introduced into the protein by substitution for at least one amino acid selected from the group consisting of H1, S2, Q3, G4, T5, F6, T7, S8, D9, Y10, S11, Y13, L14, D15, S16, R17, R18, A19, Q20, D21, F22, V23, Q24, W25, L26, M27, N28, D29, T30, R32, N33, N35, N36, I37, A38. These amino acids can be made in the context of other OXM analogs, such as those described in U.S. Pat. No. 5,858,975. The lysine variants of the present invention can be modified with amine-reactive moieties such as amine-reactive PEGs. The amine-modified peptides can be purified from unmodified peptides by any of a number of methods known in the art such as column chromatography.

OXM also can be modified at its N-terminus using methods described in the art. The modified OXM proteins can be tested for in vitro and in vivo biological activity using methods well known in the art.

Example 18. GIP

Gastric inhibitory peptide (GIP) is a small 42 amino acid peptide secreted by the intestine. GIP increases insulin secretion by the pancreas and may prove useful for treating diabetes. The amino acid sequence of GIP is represented herein by SEQ ID NO:16. A cysteine residue can be added preceding the first amino acid, Y1, or following the last amino acid Q42. A cysteine residue also can be introduced into the protein by substitution for at least one amino acid selected from the group consisting of Y1, A2, E3, G4, T5, F6, I7, S8, D9, Y10, S11, I12, A13, M14, D15, K16, I17, H18, Q19, Q20, D21, F22, V23, N24, W25, L26, L27, A28, Q29, K30, G31, K32, K33, N34, D35, W36, K37, H38, N39, I40, T41, and Q42. These amino acids can be made in the context of other native sequence GIP or GIP agonist and antagonist analogs, such as those described in U.S. Pat. Nos. 6,410,508, 6,921,748 and 7,091,183 and in Green et al. Curr. Pharm. Des. 2004, v 10, pages 3651-3662; Irwin et al. (2006) Biochem Pharmacol v. 72: pages 719-728; Alana et al. (2006) J. Biol. Chem. 281: 16370-16376; Gault et al. (2002) Biochem J. v 367: 913-920; Gault et al. (2003) J. Endocrinology v. 176: pages 133-141. A preferred analog is one that prevents cleavage of Y1 and A2 from the peptide by proteases. A preferred analog is one in which E3 is substituted with a non-glutamic acid amino acid that prevents cleavage of Y1 and A2 from the peptide. A preferred antagonist analog is one in which E3 is substituted with proline. The cysteine variants of the present invention can be modified with cysteine-reactive moieties such as cysteine reactive PEGs. The cysteine-modified peptides can be purified from unmodified peptides by any of a number of methods known in the art such as column chromatography.

Alternatively, GIP can be modified with an amine-reactive moiety at its N-terminus or at one or all of the lysine residues K16, K30, K32, K33 and K37. To make the modification reaction specific for a particular lysine residue, K16, K30, K32, K33 or K37 can be changed to a non-lysine amino acid, preferably arginine, and the mutant protein modified with an amine-reactive moiety at the remaining lysine residue. Additionally, all of the lysine residues, K16, K30, K32, K33 and K37 can be changed to non-lysine residues, preferably arginine residues, and a new lysine residue introduced into the protein. The new lysine residue can be added preceding the first amino acid, Y1, or following the last amino acid Q42. A lysine residue also can be introduced into the protein by substitution for at least one amino acid selected from the group consisting of Y1, A2, E3, G4, T5, F6, I7, S8, D9, Y10, S11, I12, A13, M14, D15, I17, H18, Q19, Q20, D21, F22, V23, N24, W25, L26, L27, A28, Q29, G31, N34, D35, W36, H38, N39, I40, T41, and Q42. These amino acids can be made in the context of native sequence GIP or GIP agonist and antagonist analogs, such as those described in U.S. Pat. Nos. 6,410,508, 6,921,748 and 7,091,183 and in Green et al. Curr. Pharm. Des. 2004, v 10, pages 3651-3662; Irwin et al. (2006) Biochem Pharmacol v. 72: pages 719-728; Alana et al. (2006) J. Biol. Chem. 281: 16370-16376; Gault et al. (2002) Biochem J. v 367: 913-920; Gault et al. (2003) J. Endocrinology v. 176: pages 133-141. The lysine variants of the present invention can be modified with amine-reactive moieties such as amine-reactive PEGs. The amine-modified peptides can be purified from unmodified peptides by any of a number of methods known in the art such as column chromatography.

GIP also can be modified at its N-terminus using methods described in the art. The modified GIP proteins can be tested for in vitro and in vivo biological activity using methods well known in the art.

Example 19. Amylin

Amylin is a 37 amino acid peptide that is cosecreted with insulin by the pancreas in response to food intake. Amylin plays a role in maintaining proper glucose levels by inhibiting glucagon secretion under conditions of hyperglycemia. Amylin also slows gastric emptying and promotes satiety, and thus may play a role in feeding and nutrition disorders. The amino acid sequence of amylin is represented herein by SEQ ID NO:17. Amylin contains two native cysteine at positions 2 and 7. These two cysteines form a disulfide bond. The carboxy-terminal tyrosine residue normally is amidated. A cysteine residue can be added preceding the first amino acid, K1, or following the last amino acid Y37. A cysteine residue also can be introduced into the protein by substitution for at least one amino acid selected from the group consisting of K1, N3, T4, A5, T6, A8, T9, Q10, R11, L12, A13, N14, F15, L16, V17, H18, S19, S20, N21, N22, F23, G24, A25, I26, L27, S28, S29, T30, N31, V32, G33, S34, N35, T36, Y37. These amino acids can be made in the context of other amylin analogs, such as those described in U.S. Pat. Nos. 5,367,052, 5,686,411, 6,087,334, and 6,610,824. The cysteine variants of the present invention can be modified with cysteine-reactive moieties such as cysteine reactive PEGs. The cysteine-modified peptides can be purified from unmodified peptides by any of a number of methods known in the art such as column chromatography.

Alternatively, amylin can be modified with an amine-reactive moiety at its N-terminus K1. A lysine residue can be added preceding the first amino acid, K1, or following the last amino acid Y37. A lysine residue also can be introduced into the protein by substitution for at least one amino acid selected from the group consisting of C2, N3, T4, A5, T6, C7, A8, T9, Q10, R11, L12, A13, N14, F15, L16, V17, H18, S19, S20, N21, N22, F23, G24, A25, I26, L27, S28, S29, T30, N31, V32, G33, S34, N35, T36, Y37. These amino acids can be made in the context of native sequence amylin or amylin analogs, such as those described in U.S. Pat. Nos. 5,367,052, 5,686,411, 6,087,334, and 6,610,824. These amino acid changes can be made in the context of native sequence amylin or a variant in which K1 is changed to a non-lysine amino acid, preferably arginine. The lysine variants of the present invention can be modified with amine-reactive moieties such as amine-reactive PEGs. The lysine-modified peptides can be purified from unmodified peptides by any of a number of methods known in the art such as column chromatography.

The peptides of the preceding Examples 11-19 can be synthesized by chemical methods or expressed as recombinant proteins using recombinant DNA technology. Methods for expressing and/or refolding proteins containing added or unpaired cysteine residues are described in U.S. Pat. Nos. 6,753,165, 7,153,943 and 7,306,931 and in U.S. Patent Publication Nos. PCT/US01/16088 and US 20070111240, all of which are incorporated herein by reference. In a preferred embodiment, bioactive peptides having free cysteines and lacking essential disulfides are refolded using the novel method of refolding a protein or peptide as described in detail herein.

REFERENCES

Abuchowski, A., Kazo, G. M., Verhoest, C. R., Van Es, T., Kafkewitz, D., Nucci, M. L., Viau, A. T. and Davis, F. F. (1984) Cancer Biochem. Biophys. 7: 175-186. Cancer therapy with chemically modified enzymes: antitumor properties of polyethylene glycol-asparaginase.

Anthony, L. S., Ghadirian, E., Nestel, F. P., and Kongshavn, P. A. (1989) Microb Pathog. 7(6):421-428. The requirement for gamma interferon in resistance of mice to experimental tularemia.

Arakawa, T., Alton, N. K., and Hsu, Y. R. (1985) J. Biol. Chem. 260: 14435-14439. Preparation and Characterization of Recombinant DNA-derived Human Interferon-γ.

Arakawa, T., Horan, T. and Rohde, M. (1990) J. Interferon Res. 10:321-329. Effect of amino-terminal processing of *Staphylococcus aureus* V-8 protease on activity and structure of recombinant IFN-γ.

Bailon, P, Palleroni, A, Schaffer, C A, Spence, C L, Fung, W J, Porter, J E, Ehrlich, G K, Pan, W, Xu, Z X, Modi, M W, Farid, A, Berthold, W, and Graves M. (2001) Bioconjug Chem. 12(2):195-202. Rational design of a potent, long-lasting form of interferon: a 40 kDa branched polyethylene glycol-conjugated interferon alpha-2a for the treatment of hepatitis C.

Beldarrain, A., Lopez-Lacomba, J., Furrazola, G. Barberia, D. and Cortijo, M. (1999) Biochem. 38:7865-7873. Thermal Denaturation of human gamma interferon. A calorimetric and spectroscopic study.

Burke, F. Smith, P., Crompton, M. Upton, C. and Balkwill, F. (1999) British J. of Cancer 80:1236-1244. Cytotoxic response of ovarian cancer cell lines to IFN-γ is associated with sustained induction of IRF-1 and p21 mRNA.

Chen, S., Isu, A., Baughman, R., Farraioloa, B. et al., (1990) J. Interferon Res. 10:S125. Pharmacokinetic disposition of recombinant human interferon-gamma following intravenous, subcutaneous and intramuscular administration in normal, male volunteers.

Cox, G. N., Doherty, D. H. and Rosendahl, M. S. (2001) U.S. Pat. No. 6,735,165. Methods for making proteins containing free cysteine residues Cunningham, B. C., Ultsch, M., de Vos, A. M., Mulkerrin, M. G., Clauser, K. R. and Wells, J. A. (1991) Science 254: 821-825. Dimerization of the extracellular domain of the human growth hormone receptor by a single hormone molecule.

Delgado, C. Francis, G E, and Derek (1992) Critical Rev Ther Drug Carrier Sys 9:249-304. The uses and properties of PEG-linked proteins.

Deiters, A, Cropp, T A, Summerer, D, Mukherji, M, and Schultz, P G. (2004) Bioorg Med Chem Lett. 14(23): 5743-5745 Site-specific PEGylation of proteins containing unnatural amino acids.

Ealick, S. E., Cook, W. J., Vijay-Kumar, S., Carson, M., Nagabhushan, T. L., Trotta, P. P. and Bugg, C. E. (1991) Science. 252: 698-702. Three-dimensional structure of recombinant human interferon-gamma.

Evinger M. and Pestka, S. (1981) Methods Enzymol. 79(Pt B): 362-368. Assay of growth inhibition in lymphoblastoid cell cultures.

Fee, C. (2003) Biotech and Bioeng. 82:200-206. Size-exclusion reaction chromatography: A new technique for protein pegylation Fleischmann, W R Jr, Masoor, J, Wu, T Y and Fleischmann C M. (1998) J Interferon Cytokine Res. 18(1):17-20. Orally administered IFN-alpha acts alone and in synergistic combination with intraperitoneally administered IFN-gamma to exert an antitumor effect against B16 melanoma in mice.

Flynn, J. L., Chan, J., Triebold, K. J., Dalton, D. K., Stewart, T. A. and Bloom, B. R. (1993) J Exp Med 178:2249-2254. An essential role for interferon gamma in resistance to *Mycobacterium tuberculosis* infection.

Foser, S, Schacher, A, Weyer, K A, Brugger, D, Dietel, E, Marti, S and Schreitmuller T. (2003) Protein Expr Purif. 30(1):78-87. Isolation, structural characterization, and antiviral activity of positional isomers of monopegylated interferon alpha-2a (PEGASYS).

Harris, J. M. and Chess, R. B. (2003) Nat Rev. Drug Discov 2:214-221. Effect of PEGylation on pharmaceuticals.

Higuchi, R. (1990) in "PCR Protocols" (M A Innis, D H Gelfand, J J Sninsky, & T J White, eds.) Academic Press 177-83 "Recombinant PCR"

Hooftman, G., Herman, S., and Schacht, E. (1996) J. Bioactive Compatible Polymer 11:135-139. PEGs with reactive endgroups II. Practical consideration for the preparation of protein-PEG conjugates.

Horoszewicz, J. S., Leong, S. S. and Carter, W. A. (1979) Science 206(4422): 1091-1093. Noncycling tumor cells are sensitive targets for the antiproliferative activity of human interferon.

Keating, M. J., Holmes, R., Lerner, S. and Ho, D. H. (1993) Leuk. Lymphoma 10, 153. L-asparaginase and PEG asparaginase—past, present, and future.

Key, L L, Jr, Rodriguiz, R M, Willi, S M, Wright, N M, Hatcher, H C, Eyre, D R, Cure, J K, Griffin, P P and Ries, W L. (1995) N Engl J Med. 332(24):1594-1559. Long-term treatment of osteopetrosis with recombinant human interferon gamma.

Kita, Y. Rohde, M. F., Arakawa, T. Fagin K. D., Fish, E. N. and Banerjee, K. (1990) Drug Des. Deliv. 6:157-167. Characterization of a polyethylene glycol conjugate of recombinant human interferon-gamma.

Jackson, S. H., J. I. Gallin, and S. M. Holland. (1995) J. Exp. Med. 182:751-758. The p47$^{phox}$ mouse knock-out model of chronic granulomatous disease.

Jackson, S H, Miller G F, Segal B H, Mardiney M 3rd, Domachowske, J B, Gallin, J I, and Holland S M. (2001) J Interferon Cytokine Res. 21(8):567-73. IFN-gamma is effective in reducing infections in the mouse model of chronic granulomatous disease (CGD).

Larkin, J, Jin, L, Farmen, M, Venable, D, Huang, Y, Tan, S L, and Glass J I. (2003) J Interferon Cytokine Res.

23(5):247-57. Synergistic antiviral activity of human interferon combinations in the hepatitis C virus replicon system Lau, J. and Horvath, C. (2002) Mount Sinai Journal of Medicine 69: 156-168. Mechanisms of Type I interferon cell signaling and STAT-mediated transcription responses.

Liu, G. (2003) Abstract at the American Society of Microbiology BioDefense meeting Mar. 11, 2003.

Lundell, D., Lunn, C., Senior, M., Zavodny, P. and Narula, S. (1994) J. Biol. Chem. 269:16159-16162. Importance of the loop connecting A and B helices of human interferon-γ in recognition by interferon-γ receptor.

Malik, S. T., Knowles, R. G., East, N., Lando., D., Stamp, G., and Balkwill, F. R. (1991) Cancer Res. 51(24):6643-6649. Antitumor activity of gamma-interferon in ascitic and solid tumor models of human ovarian cancer.

Merchant M S, Yang Z, Melchionda F, Romero M, Klein R, Thiele C J, Tsokos M, Kontny H U, Mackall C L (2004) Interferon gamma enhances the effectiveness of tumor necrosis factor-related apoptosis-inducing ligand receptor agonists in a xenograft model of ewing's sarcoma.

Meyers, F. J., Paradise, C., Scudder, S. A., Goodman, G., and Konrad, M. (1991) Clin Pharmacol Ther 49:307-313. A phase I study including pharmacokinetics of polyethylene glycol conjugated interleukin-2.

Monkarsh, S., Ma, Y, Aglion, A., Bailon, P. et al. (1997) Anal. Biochem. 247:434-440. Positional isomers of monoPEGylated Interferon alpha: Isolation, characterization and biological activity.

Morpurgo, M. and Veronese, F. (2004) in Methods in Molecular Biology 283: 45-70. Conjugates of Peptides and Proteins to Polyethylene Glycols.

Mosmann, T. (1983) J. Immunol Methods 65(1-2):55-63. Rapid colorimetric assay for cellular growth and survival: application to proliferation and cytotoxicity assays.

Mulkerrin, M. G. and Wetzel, R. (1989) Biochemistry 28:6556-6561. pH dependence of the reversible and irreversible thermal denaturation of gamma-interferons.

Murray, H. W. (1990) J Infect Dis 161:992-994. Effect of continuous administration of interferon-γ in experimental visceral leishmaniasis.

Nagata, K., Kikuchi, N., Ohara, O., Teraoka, H., Yoshida, N., Kawade, Y. (1986) FEBS Lett. 1205(2):200-204. Purification and characterization of recombinant murine immune interferon.

Pace, J., Russell, S. LeBlanc, P., Murasko, D. (1985) J. Immunol. 134:977-981. Comparative effects of various classes of mouse interferons on macrophage activation for tumor cell killing.

Sato, H. (2002) Adv. Drug Deliv. Rev 54:487-509. Enzymatic procedure for site-specific PEGylation of proteins.

Scharf, S. J. in "PCR Protocols" (M A Innis, D H Gelfand, J J Sninsky, & T J White, eds.) Academic Press (1990) pp. 84-91 "Cloning with PCR"

Sheffield, W. P. (2001) Current Drug Targets 1: 1-10 Modification of Clearance of Therapeutic and Potentially Therapeutic Proteins Sims, G. and Snap, T. (1980) Anal. Biochem. 107:60-63. A method for the estimation of polyethylene glycol in plasma protein fractions.

Summers S A, Dorling A, Boyle J J, and Shaunak S. (2005) Am J Transplant, 5(8):2067-2069. Cure of disseminated cryptococcal infection in a renal allograft recipient after addition of gamma-interferon to anti-fungal therapy.

Tang, W. Chang, Y, Xu, L. F. Zheng, Z. C. and Liu, X. Y (1996) Shen Wu Hua Xue Yu Sheng Wu Wu Li Xue Bao 28:312-315. Studies on the PEGylation of Protein at a Specific Site: Sulfhydryl-PEGylation of 97Cys IFN-gamma.

Van Den Hazel, B., Jensen, A., Nygaard, F. Andersen, K. (2005) U.S. Pat. No. 6,958,388. Interferon gamma polypeptide variants Wall, L., Burke, F. Smyth, J. and Balkwill, F. (2003) Gynecol. Oncol. 88, 149-151. The anti-proliferative activity of interferon-γ on ovarian cancer: In vitro and in vivo.

Walter, M. R., Windsor, W. T., Nagabhushan, T. L., Lundell, D. J., Lunn, C. A., Zauodny, P. J. and Narula, S. K. (1995) Nature 376:230-235. Crystal structure of a complex between interferon-gamma and its soluble high-affinity receptor.

Weiss, A., Wiskocil, R. L. and Stobo, J. D. (1984) J. Immunology 133: 123-128. The role of T3 in the activation of human T cells.

Wheelock, E. F. (1965) *Science* 149:310-311. Interferon-like virus-inhibitor induced in human leukocytes by phytohgemagglutinin.

Wisckocil, R., Weiss, A., Imboden, J., Kamin-Lewis, R. a. and Stobo, J. (1985) J. Immunology 134: 1599-1603. Activation of a human T cell line: a two-stimulus requirement in the pretranslational events involved in the coordinate expression of interleukin 2 and gamma-interferon genes.

Yanai, Y., Sanou, O., Kayano, T., Ariyasu, H., Yamamoto, K., Yamauchi, H., Ikegami, H., and Kurimoto, M. (2001) J Interferon Cytokine Res. 21(10):835-841. Analysis of the antiviral activities of natural IFN-alpha preparations and their subtype compositions.

Yang, X, Merchant M S, Romero, M E, Tsokos, M, Wexler L H, Kontny U, Mackall C L, Thiele C J (2003) Induction of Caspase 8 by interferon gamma renders some neuroblastoma (NB) cells sensitive to tumor necrosis factor-related apoptosis-inducing ligand (TRAIL) but reveals that lack of membrane TR1/Tr2 also contributes to TRAIL resistance in NB.

Younes, H. and Amsden, B. (2002) J. Pharm Sci. 91: 2-17. Interferon-gamma therapy: Evaluation of routes of administration and delivery systems.

Zavodny, P. J., Petro, M. E., Chiang, T. R, Narula, S. K., Leibowitz, P. J. (1988) J Interferon Res. 8:483-94. Alterations of the amino terminus of IFN-γ □expression and biological activity.

Zalispky, S. (1995) Adv. Drug Delivery Rev 16:157-182. Chemistry of polyethylene glycol conjugates with biologically active molecules.

PCT Publication No. WO 99/03887, published Jan. 28, 1999.

PCT Publication No. WO 00/42175, published Jul. 20, 2000.

PCT Publication No. WO 01/87925, published Nov. 22, 2001.

Each publication cited herein is incorporated herein by reference in its entirety.

Each of the following applications is incorporated herein by reference in its entirety: U.S. Provisional Application Ser. No. 60/870,022, filed Dec. 14, 2006; U.S. patent application Ser. No. 10/773,530, filed Feb. 5, 2004; U.S. Pat. Nos. 7,148,333; 6,608,183; PCT Application Serial No. PCT/US98/14497, filed Jul. 13, 1998; and U.S. Provisional Application Ser. No. 60/052,516, filed Jul. 14, 1997.

While various embodiments of the present invention have been described in detail, it is apparent that modifications and adaptations of those embodiments will occur to those skilled in the art. It is to be expressly understood, however, that such modifications and adaptations are within the scope of the present invention, as set forth above and in the following claims.

What is claimed is:

1. A cysteine analog of exendin-4 (SEQ ID NO:11), wherein a cysteine residue is added to the peptide either by substitution for a native amino acid in exendin-4 or by insertion preceding the first amino acid of exendin-4 or following the last amino acid of exendin-4, wherein the cysteine residue substituted for the native amino acid is selected from the group consisting of H1, G2, E3, G4, T7, S8, D9, S11, Q13, M14, E15, F22, I23, W25, L26, and K27.

2. The cysteine analog of claim 1, wherein a cysteine residue is inserted preceding the first amino acid of exendin-4.

3. The cysteine analog of claim 1, wherein a cysteine residue is inserted following the last amino acid of exendin-4.

4. The cysteine analog of claim 1, wherein the added cysteine residue is modified with a cysteine reactive moiety selected from the group consisting of: a polyethylene glycol, a polyvinyl pyrolidone, a carbohydrate, a dextran, a sugar, a starch, a peptide, a lipid, a label, a dye, a polymer, a chromophore, and a radionucleotide.

5. The cysteine analog of claim 4, wherein the reactive group on the cysteine-reactive moiety is selected from the group consisting of a maleimide group, a vinylsulfone group, and an iodoacetamide group.

6. The cysteine analog of claim 1, wherein the added cysteine residue is modified with a polyethylene glycol.

7. The cysteine analog of claim 6, wherein the polyethylene glycol moiety is selected from the group consisting of a linear polyethylene glycol and a branched polyethylene glycol.

8. The cysteine analog of claim 1, wherein the added cysteine residue is modified with a lipid.

9. The cysteine analog of claim 1, wherein the added cysteine residue is modified with a sugar.

10. The cysteine analog of claim 1, wherein the cysteine analog of exendin-4 is synthesized by chemical methods.

11. The cysteine analog of claim 1, wherein the cysteine analog of exendin-4 is a recombinant protein.

12. The cysteine analog of claim 4, wherein the cysteine analog is exposed to a cysteine-reactive moiety to obtain a cysteine-modified protein, wherein the step of exposing is conducted in the presence of a reducing agent.

13. The cysteine analog of claim 1, wherein the cysteine analog is selected from the group consisting of a homologue of exendin-4 and a truncated form of exendin-4.

14. A composition comprising the cysteine analog of claim 1 and a pharmaceutical accepted carrier.

* * * * *

SEQUENCE LISTING

<160> NUMBER OF SEQ ID NOS: 17

<210> SEQ ID NO 1
<211> LENGTH: 143
<212> TYPE: PRT
<213> ORGANISM: Homo sapiens

<400> SEQUENCE: 1

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140

<210> SEQ ID NO 2
<211> LENGTH: 133
<212> TYPE: PRT
<213> ORGANISM: Mus musculus

<400> SEQUENCE: 2

His Gly Thr Val Ile Glu Ser Leu Glu Ser Leu Asn Asn Tyr Phe Asn
1               5                   10                  15

Ser Ser Gly Ile Asp Val Glu Glu Lys Ser Leu Phe Leu Asp Ile Trp
            20                  25                  30

Arg Asn Trp Gln Lys Asp Gly Asp Met Lys Ile Leu Gln Ser Gln Ile
        35                  40                  45

Ile Ser Phe Tyr Leu Arg Leu Phe Glu Val Leu Lys Asp Asn Gln Ala
    50                  55                  60

Ile Ser Asn Asn Ile Ser Val Ile Glu Ser His Leu Ile Thr Thr Phe
65                  70                  75                  80

Phe Ser Asn Ser Lys Ala Lys Lys Asp Ala Phe Met Ser Ile Ala Lys
                85                  90                  95

Phe Glu Val Asn Asn Pro Gln Val Gln Arg Gln Ala Phe Asn Glu Leu
            100                 105                 110

Ile Arg Val Val His Gln Leu Leu Pro Glu Ser Ser Leu Arg Lys Arg
        115                 120                 125

Lys Arg Ser Arg Cys
    130

<210> SEQ ID NO 3
<211> LENGTH: 36
<212> TYPE: DNA
<213> ORGANISM: Artificial
<220> FEATURE:
<223> OTHER INFORMATION: synthetic primer -continued

<400> SEQUENCE: 3
cgcaagcttg ccaccatgaa atatacaagt tatatc                                36

<210> SEQ ID NO 4
<211> LENGTH: 36
<212> TYPE: DNA
<213> ORGANISM: Artificial
<220> FEATURE:
<223> OTHER INFORMATION: synthetic primer

<400> SEQUENCE: 4
cgcggatcct ccggactggg atgctcttcg accttg                                36

<210> SEQ ID NO 5
<211> LENGTH: 36
<212> TYPE: DNA
<213> ORGANISM: Artificial
<220> FEATURE:
<223> OTHER INFORMATION: synthetic primer

<400> SEQUENCE: 5
caggacccat acgtaaaaga agcagaaaac cttaag                                36

<210> SEQ ID NO 6
<211> LENGTH: 39
<212> TYPE: DNA
<213> ORGANISM: Artificial
<220> FEATURE:
<223> OTHER INFORMATION: synthetic primer

<400> SEQUENCE: 6
ccggaattct tactgggatg cacgtcgacc ttgaaacag                              39

<210> SEQ ID NO 7
<211> LENGTH: 49
<212> TYPE: DNA
<213> ORGANISM: Artificial
<220> FEATURE:
<223> OTHER INFORMATION: synthetic primer

<400> SEQUENCE: 7
cgcggatcca tcttggagga tgattaaatg caggacccat acgtaaaag                  49

<210> SEQ ID NO 8
<211> LENGTH: 29
<212> TYPE: PRT
<213> ORGANISM: Homo sapiens

<400> SEQUENCE: 8

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 9
<211> LENGTH: 31
<212> TYPE: PRT
<213> ORGANISM: Homo sapiens

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly

<210> SEQ ID NO 10
<211> LENGTH: 33
<212> TYPE: PRT
<213> ORGANISM: Homo sapiens

<400> SEQUENCE: 10

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 11
<211> LENGTH: 39
<212> TYPE: PRT
<213> ORGANISM: Homo sapiens

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 12
<211> LENGTH: 36
<212> TYPE: PRT
<213> ORGANISM: Homo sapiens

<400> SEQUENCE: 12

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 13
<211> LENGTH: 28
<212> TYPE: PRT
<213> ORGANISM: Homo sapiens

<400> SEQUENCE: 13

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 14
<211> LENGTH: 37
<212> TYPE: PRT
<213> ORGANISM: Homo sapiens

<400> SEQUENCE: 14

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Lys Asn Asn Ile Ala
        35

<210> SEQ ID NO 15
<211> LENGTH: 10
<212> TYPE: PRT
<213> ORGANISM: Artificial
<220> FEATURE:
<223> OTHER INFORMATION: synthetic peptide

<400> SEQUENCE: 15

Asp Thr Lys Arg Asn Lys Asn Asn Ile Ala
1               5                   10

<210> SEQ ID NO 16
<211> LENGTH: 42
<212> TYPE: PRT
<213> ORGANISM: Homo sapiens

<400> SEQUENCE: 16

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 17
<211> LENGTH: 37
<212> TYPE: PRT
<213> ORGANISM: Homo sapiens

<400> SEQUENCE: 17

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35
```